US010603351B2

(12) United States Patent
Bell et al.

(10) Patent No.: US 10,603,351 B2
(45) Date of Patent: Mar. 31, 2020

(54) ENGINEERED SYNERGISTIC ONCOLYTIC VIRAL SYMBIOSIS

(75) Inventors: John C. Bell, Ottawa (CA); Fabrice Le Boeuf, Ottawa (CA)

(73) Assignee: TURNSTONE LIMITED PARTNERSHIP, Toronto (CA)

( * ) Notice: Subject to any disclaimer, the term of this patent is extended or adjusted under 35 U.S.C. 154(b) by 0 days.

(21) Appl. No.: 13/060,028

(22) PCT Filed: Aug. 20, 2009

(86) PCT No.: PCT/CA2009/001176
§ 371 (c)(1),
(2), (4) Date: May 16, 2011

(87) PCT Pub. No.: WO2010/020056
PCT Pub. Date: Feb. 25, 2010

(65) Prior Publication Data
US 2011/0206640 A1 Aug. 25, 2011

Related U.S. Application Data

(60) Provisional application No. 61/136,251, filed on Aug. 21, 2008.

(51) Int. Cl.
A61K 38/16 (2006.01)
A61K 35/766 (2015.01)
A61K 35/768 (2015.01)
A61K 38/19 (2006.01)
A61K 35/76 (2015.01)

(52) U.S. Cl.
CPC ............ A61K 38/162 (2013.01); A61K 35/76 (2013.01); A61K 35/766 (2013.01); A61K 38/193 (2013.01); C12N 2710/24132 (2013.01); C12N 2760/20232 (2013.01)

(58) Field of Classification Search
CPC .... A61K 35/76; A61K 38/162; A61K 38/193; A61K 35/766; A61K 2300/00
See application file for complete search history.

(56) References Cited

U.S. PATENT DOCUMENTS

| 2003/0031681 | A1  | 2/2003  | McCart et al. |            |
|--------------|-----|---------|---------------|------------|
| 2003/0044384 | A1* | 3/2003  | Roberts et al.| 424/93.2   |
| 2004/0044185 | A1* | 3/2004  | Duncan ........| 530/350    |
| 2007/0098743 | A1* | 5/2007  | Bell ..........| A61K 39/205 424/224.1 |
| 2009/0317456 | A1* | 12/2009 | Karrasch et al.| 424/450   |

FOREIGN PATENT DOCUMENTS

| EP | 1 218 019 B1   |   | 3/2006  |
|----|----------------|---|---------|
| WO | 1999-29343 A1  |   | 6/1999  |
| WO | WO 00/73479    | * | 7/2000  |
| WO | 2001/095919 A2 |   | 12/2001 |
| WO | 2004/085658 A1 |   | 10/2004 |
| WO | WO 2005/007824 | * | 1/2005  |
| WO | 2007-093036 A1 |   | 8/2007  |
| WO | WO/2007/093036 | * | 8/2007  |
| WO | WO2008043576   | * | 4/2008  |

OTHER PUBLICATIONS

Wu et al., Oncolytic efficacy of recombinant vesicular stomatitis virus and myxoma virus in experimental models of rhabdoid tumors, Clin Cancer Res. 14(4):1218-27, 2008.*
Alcami et al J Virol. 2000 ; 74(23): 11230-11239.*
Stojdl et al Cancer Cell, 2003, 4: 263-275.*
Carillo et al Infection. Genetics and Eyolution, 2008. 8(5), 614-620.*
Brown et al Journal of Virology, 2009, 83(2), 552-561.*
Lichty et al, Journal of Virology 87:3379-3384, 2006.*
Gnant et al (Annals of Surgery, 1999, 230, 3, 352-361.*
Chernajovsky et al BMJ. 2006; 332(7534): 170-2.*
Zhang et al (Cancer Res. 2007, 67, 10038-10046.*
Gentschev et al Apr. 2009;16(4):320-8.*
Brun et al Molecular Therapy (2010) 18 8, 1440-1449.*
McCart et al Cancer Res. 2001, 8751-8757.*
Sanjuan PNAS, 2004, 101, 15376-15379, pp. 1-3 of suppl info.*
Ahmed et al Journal of Virology, 4646-4657 (Year: 2003).*
Brun, J., et al., "Identification of Genetically Modified Maraba Virus as an Oncolytic Rhabdovirus," Molecular Therapy, vol. 18, No. 8, pp. 1440-1449 (Aug. 2010).
European Search Report and European Supplementary Search Report for European Patent Application No. 09807799.3 dated Aug. 20, 2012, statement considered.

* cited by examiner

Primary Examiner — Anoop K Singh
(74) Attorney, Agent, or Firm — Polsinelli PC; Christopher M. Cabral

(57) ABSTRACT

In one aspect, the invention provides methods for preferentially killing target proliferating cells in a host, such as cancer cells, by infecting host tissues with two or more strains of virus. The strains of virus may be selected to provide a synergistic and symbiotic effect, involving a contemporaneous lytic infection in the target proliferating cells. In selected embodiments, the viruses are selected so that expression of a first virulence factor in proliferating cells infected with the first virus increases the lytic effect of the second virus; and, expression of the second virulence factor in proliferating cells infected with the second virus increases the lytic effect of the first virus. The genomes of the first and second viruses may be selected so that they are incompatible for recombination between the viral genomes in cells of the host.

6 Claims, 8 Drawing Sheets
Specification includes a Sequence Listing.

FIG. 4

ENGINEERED SYNERGISTIC ONCOLYTIC VIRAL SYMBIOSIS

The present application is a national phase application under 35 U.S.C. § 371 of International Patent Application PCT Application No. PCT/CA2009/001176, filed Aug. 20, 2009, which claims the benefit of U.S. Provisional Application No. 61/136,251 filed Aug. 21, 2008. The entire contents of these applications are incorporated by reference.

SEQUENCE LISTING SUBMISSION VIA EFS-WEB

A computer readable text file, entitled "13060028_ST25.txt," created on or about Mar. 1, 2013, with a file size of about 6 KB, contains the sequence listing for this application and is hereby incorporated by reference in its entirety.

FIELD

The invention is in the field of cancer treatment, particularly oncolytic viral therapies.

BACKGROUND

Oncolytic viruses are generally selected or engineered to grow inside cancer cells preferentially, as compared with normal cells (Kim et al., 2001). A wide variety of oncolytic viruses have been used in preclinical and clinical cancer therapies (see Parato et al., 2005; Bell et al, 2003; Everts and van der Poel, 2005; Ries and Brandts, 2004). These viruses can cause tumor cell death through direct replication-dependent and/or viral gene expression-dependent oncolytic effects (Kim et al., 2001). In addition, viruses may be able to enhance the induction of cell-mediated antitumoral immunity within the host (Todo et al., 2001; Sinkovics et al., 2000). These viruses also can be engineered to expressed therapeutic transgenes within the tumor to enhance antitumoral efficacy (Hermiston, 2000).

Oncolytic viruses that have been selected or engineered to productively infect tumour cells include adenovirus (Xia et al., 2004; Wakimoto et al., 2004); reovirus; herpes simplex virus 1 (Shah, et al., 2003); Newcastle disease virus (NDV; Pecora, et al., 2002); vaccinia virus (VV; Mastrangelo et al., 1999; US 2006/0099224); coxsackievirus; measles virus; vesicular stomatitis virus (VSV; Stojdl, et al., 2000; Stojdl, et al., 2003); Seneca Valley Virus (Reddy, et al. 2007), influenza virus; myxoma virus (Myers, R. et al., 2005).

A variety of mechanisms have been suggested for mediating tumor selectivity in oncolytic therapies. Methods of targeting oncolytic viruses to cancer cells may, for example, be based on differential expression of receptors. An unmodified cocksackie virus (CAV21) is thought to selectively target cancer cells because the viral receptors ICAM-1 and DAF are overexpressed on malignant melanoma cells. WO 2005/087931 discloses selected Picornavirus adapted for lytically infecting a cell in the absence of intercellular adhesion molecule-1 (ICAM-1). Engineering to alter specificity of receptors is also possible to enhance tumor-targeting of onocolytic viruses including adenovirus (Sebestyen 2007, Carette 2007) and measles (Allen 2006, Hasegawa 2006), for example.

Alterations in cancer cell signalling pathways lead to the upregulation of genes required for cell proliferation, such as thymidine kinase (TK) and ribonucleotide reductatase (RNR) which are required for the production of dNTPs used in DNA synthesis. The replication of viruses can be restricted to cancer cells with high TK or RNR activity by deleting the viral versions of TK or RNR, or other genes upregulated in cancer cells. U.S. Pat. No. 7,208,313 discloses a VV with TK and VGF deletions and WO 2005/049845, WO 2001/053506, US 2004/120928, WO 2003/082200, EP 1252323 and US 2004/9604 disclose herpes viruses such as HSV, which may have improved oncolytic and/or gene delivery capabilities.

The Ras/PRK pathway is commonly mutated in cancer cells. This pathway affects the interferon (IFN) response pathway, which is thought to be deficient in cancer cells with activated Ras. Some oncolytic viruses are tumor-selective based on the difference in the innate immune response pathway in normal vs. cancer cells. For example, unmodified reovirus is naturally selective to cancer cells based on the lack of innate anti-viral response in tumor cells with activations in the Ras/PRK pathway. WO 2005/002607 discloses the use of oncolytic viruses to treat neoplasms having activated PP2A-like or Ras activities, including combinations of more than one type and/or strain of oncolytic viruses, such as reovirus. It has been suggested that sensitivity to a host interferon response is a desirable characteristic for oncolytic viruses. For example, WO 2004/014314 suggests that poxviruses, including vaccinia virus, may be adapted for use to treat cancers by introducing mutations in genes encoding interferon binding proteins.

Susceptibility to an anti-viral response may, however, confer safety benefits on an oncolytic virus. For example, intranasal infection of mice with VSV has been shown to lead to lethal infection of the CNS. This serious adverse effect may be addressed by combined treatment with interferon and VSV (Stojdl et al., 2003). In an effort to find additional mechanisms to address the risks posed by therapeutic uses of systemic VSV infection, VSV strains have been developed that have a heightened sensitivity to a host interferon-mediated anti-viral response. In particular, amino acid substitutions in the matrix (M) protein gene of VSV, such as VSVdeltaM51 (Lun et al., Journal of the National Cancer Institute 2006 98(21):1546-1557), may be stronger inducers of the host interferon response, and may be vulnerable to the intact interferon response of normal cells but not to the attenuated interferon response of cancer cells which are deficient in IFN response pathways. EP 1218019, US 2004/208849, US 2004/115170, WO 2001/019380, WO 2002/050304, WO 2002/043647 and US 2004/170607 disclose oncolytic viruses, such as Rhabdovirus, picornavirus, and VSV, in which the virus may exhibit differential susceptibility to a host interferon response, with selectivity for tumor cells having low PKR activity.

VV expresses a repertoire of mechanisms for evading host anti-viral responses. At least partly as a consequence of these attributes, VV infection of an immunocompromised host can lead to serious and lethal complications, such as systemic vaccinia infection with encephalitis (Lane, et al., 1969; Arita, et al., 1985). To address the risks entailed in systemic use of wild type VV, strains have been developed that have deficits in various aspects of the VV infection pathway. For example, VV may be engineered to lack thymidine kinase (TK) activity. A TK-strain of VV requires thymidine triphosphate for DNA synthesis, which leads to preferential replication in dividing, and hence cancerous, cells. In an alternative approach, VV strains may be engineered to lack vaccinia virus growth factor (VGF). This secreted protein is produced early in the VV infection process, acting as a mitogen to prime surrounding cells for VV infection (Buller et al., 1988, Virology 164: 182-192). Combined strains of VV having both TK and VGF deficits benefit from the enhanced safety and specificity that results from the absence of mitogenic VGF activity in conjunction with the metabolic host cell specificity conferred by the requirement for thymidine triphophate. Similarly, vaccinia virus engineered to lack genes that normally thwart the host IFN-response (E3L, K3L, B18R, etc.) are also attenuated in normal cells but can grow in tumor cells lacking IFN-response. WO 2005/007824 discloses oncolytic vaccinia viruses and their use for selective destruction of cancer cells, which may exhibit a reduced ability to inhibit the antiviral dsRNA dependent protein kinase (PKR) and increased sensitivity to interferon. WO 2003/008586 similarly discloses methods for engineering oncolytic viruses, which involve alteration or deletion of a viral anti-PKR activity.

A number of orthopoxviruses express a type I interferon (IFN)-binding protein, which is encoded by the B18R open reading frame in the WR strain of vaccinia virus. The B18R protein has significant regions of homology with the subunits of the mouse, human, and bovine type I IFN receptors, reportedly binds human IFN2 with high affinity, and is reported to inhibit transmembrane signaling. The B18R protein reportedly exists as a soluble extracellular as well as a cell surface protein, and thus may block both autocrine and paracrine functions of IFN (Colamonici et al., 1995, JBC vol 270, pp 15974-16978). U.S. Pat. No. 7,285,526 describes therapeutic uses of B18R.

Further references that have considered oncolytic viruses within the scope of tumour biology include the following: Bell, 2007; Parato et al., 2005; Crompton et al., 2007; Russell and Peng, 2007; Park et al., 2008; Liu et al., 2008; Kim, 2001; Kumar et al., 2008; McCart et al., 2001; Parr et al., 1997; Thorne et al., 2007; Symons et al., 1995; Alcami and Smith, 1995; Colamonici et al., 1995; Alcami et al., 2000; Stojdl et al., 2000; Stojdl et al., 2003; and Lichty et al., 2004.

Abbreviations used herein include the following: eGFP, enhanced green fluorescent protein; MOI, multiplicity of infection; PFU, plaque-forming unit; FAST, Fusion Associated Small Transmembrane; SEM, standard error of the mean; DsRed, Discosoma sp. red fluorescent protein; and IU, international units.

SUMMARY

In one aspect, the invention provides methods for selectively ablating proliferating cells, such as cancer cells, in a host. The invention makes use of a combination of lytic viruses, such as oncolytic viruses, administered to the host so as to induce a contemporaneous synergistic lytic infection in the proliferating cells.

The combination of viruses may be selected so that the first lytic virus has a genome encoding a first virulence factor; and, the second lytic virus has a genome encoding a second virulence factor, wherein expression of the first virulence factor in proliferating cells infected with the first virus increases the lytic effect of the second virus; and, expression of the second virulence factor in proliferating cells infected with the second virus increases the lytic effect of the first virus. In conjunction with this combined synergistic effect, the viruses may be selected so that the genomes of the first and second viruses are incompatible for recombination in cells of the host, to reduce the likelihood that a recombinant virus will acquire the combined attributes of the selected viruses.

In some embodiments, the genome of the first virus does not encode the second virulence factor. Similarly, in some embodiments, the genome of the second virus may not encode the first virulence factor.

To render the viral genomes incompatible for recombination, the viruses may be selected so that:
the genome of the first virus is a DNA genome and the genome of the second virus is an RNA genome, and the second virus is not a Retroviridae; or,
the genome of the first virus is an RNA genome and the genome of the second virus is a DNA genome, and the first virus is not a Retroviridae; or,
the genome of the first virus is a positive sense RNA genome and the genome of the second virus is a negative sense RNA genome; or,
the genome of the first virus is a negative sense RNA genome and the genome of the second virus is a positive sense RNA genome; or,
the genome of the first virus is a double stranded RNA genome and the genome of the second virus is a single stranded RNA genome; or,
the genome of the first virus is a single stranded RNA genome and the genome of the second virus is a double stranded RNA genome.

Oncolytic viruses for use in the invention may for example be a vaccinia virus (VV), or a vesicular stomatitis virus (VSV). For example, the VV may be engineered so that it does not express functional thymidine kinase, and/or expresses GM-CSF, and/or does not express functional vaccinia growth factor, and/or lacks a functional E3L gene. The VSV may for example be engineered so that it does not express a functional matrix (M) protein for disrupting antiviral responses.

In selected embodiments, the invention provides methods of treating proliferating cells, such as a cancer, in a host, such as a human patient, which involve administering an effective amount of each of a combination of oncolytic viruses to the patient so as to induce a contemporaneous synergistic oncolytic infection of cancer cells by the viruses. The combination of viruses may for example include: a VV expressing a soluble IFN binding protein; and, a VSV expressing a membrane fusion protein. Alternatively, methods may involve treating the patient with an effective amount of a VSV expressing a reovirus Fusion Associated Small Transmembrane (FAST) protein.

In an alternative aspect, the invention provides methods of selectively ablating proliferating cells, such as cancer cells, in a host, such as a human patient, wherein the host comprises: a non-target tissue having a non-target anti-viral interferon response; and, a target tissue comprising the proliferating cells, the target tissue having a target interferon response. Such methods may include administering to the host an effective amount of at least two recombinant virus strains, a priming virus and a targeted virus, wherein infection of the target tissue by the priming virus augments a targeting virus infection of the proliferating cells by down-regulating the target interferon response, and wherein the non-target anti-viral interferon response remains effective in the non-target tissues to ameliorate infection of the non-target tissue by the targeted virus, whereby lytic infection of the targeting virus is selective for the proliferating cells of the target tissue compared to cells of the non-target tissue.

Figure 1A:
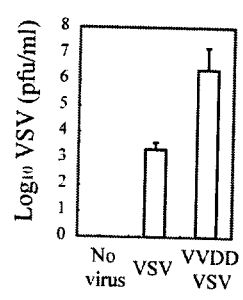
FIG. 1: Synergistic cytotoxic effects of Vaccinia (VVdd) and VSVΔ51 combination treatment on various cancer cell lines. 75% confluent HT29 colon or 786-0 renal cancer cells were left untreated or treated with VVdd-eGFP (0.1 MOI)

for 2 hours, or with VSVΔ51-DsRed (0.0001 MOI) for 45 minutes, or in combination with the two viruses, VVdd for 2 hours and 4 hours later with VSVΔ51 for the last 45 minutes. (A) Viral titers were determined after infection of HT29 cells with VSVΔ51 at 0.0001 MOI for 48 h. Supernatants were collected for standard plaque assay. Mean±SEM from 3 independent embodiments are presented. (B) Isobologram analysis: 786-0 cells were treated with serial dilutions of Vaccinia virus followed by VSV (fixed ratio of 100:1 PFU) in 96-well plates. Cytotoxicity was assessed using alamar blue reagent after 72 hours. Combination indices (CI) were calculated using Calcusyn software according to the method of Chou and Talalay. Plots represent the algebraic estimate of the CI in function of the fraction of cells affected (Fa). Error bars represent the standard deviation of the estimate. One of two independent working embodiments in quadruplicate is presented.

FIG. 2: The Vaccinia virus B18R gene product enhances vesicular stomatitis virus expression into HT29 cancer cell lines. (A) VSV titers were determined after infection of HT29 cells with VSVΔ51 at 0.0001 MOI after 48 hours. Supernatants were collected for standard plaque assay. Mean±SEM from 3 independent embodiments are presented. (B) 75% confluent HT29 colon cancer cells were left untreated or treated with VVDD-eGFP or VVDB18R-eGFP (0.1 MOI) for 2 hours alone, in combination with VSVΔ51-DsRed (0.0001 MOI) or not for 45 minutes. Viral titers were determined after infection of HT29 cells. Black and white bars are respectively VVs and VSV. Mean±SEM from 3 independent embodiments are presented. (C) Isobologram analysis: 786-0 cells were treated with serial dilutions of B18R gene product followed by VSV (fixed ratio of 1 µg:50000 PFU) in 96-well plates and processed as in FIG. 1B, detailed above. CI: Combination indices. Fa: fraction of cells affected. Error bars represent the standard deviation of the estimate. One of two independent working embodiments in quadruplicate is presented. (D) HT29 colon cancer cells were pre-treated or not with various concentration of recombinant B18R (10e-1 to 10e-6 µg) protein during 2 hours or, cells were treated with VVDD-eGFP or VVDB18R-eGFP (0.1 MOI) for 2 hours. Then, VSVΔ51-DsRed (0.0001 MOI) was added with or not various concentration of INFα (5 to 30 IU). Supernatants were collected for standard VSVΔ51 plaque assay 48 hours later. One embodiment is presented.

Figure 3A:
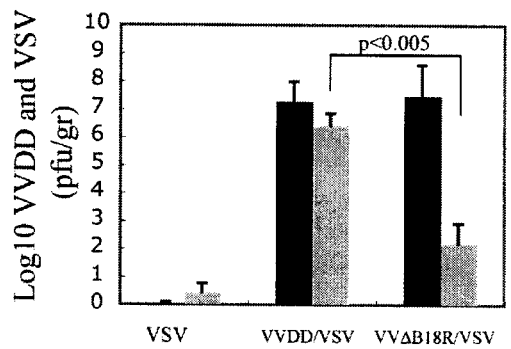

FIG. 3: Vaccinia virus enhances vesicular stomatitis virus expression into human in vivo tumour. HT29 subcutaneous xenograft tumour models were established in nude mice. After tumour growth, group received VVDD or VVΔB18R-eGFP (1.10e6 pfu) and 2 days after, VSVΔ51-Luciferease (1.10e7 pfu) was also injected intravenously. (A) In vivo tumours were homogenized and titrations were performed for each mouse of the groups. VSVΔ51 and VVΔB18R/VSVΔ51 groups contained 5 mice and VVDD/VSVΔ51 group 9 mice. Bars correspond to standard error and a T test was used to confirm statistical significance of difference between VVDD/VSVΔ51 and VVΔB18R/VSVΔ51 groups. (B) HT29 subcutaneous xenograft tumour models were established in nude mice as described herein. One and a half weeks later, viruses were injected as previously described. Size of tumour was monitored for each groups (N=4). Bars correspond to the standard deviation. (C) 4T1 subcutaneous graft tumour models were established in immunocompetent mice. One week and half later, viruses were injected as previously described. Size of tumour was monitored for each groups (N=4). Bars correspond to the standard deviation.

Figure 4:
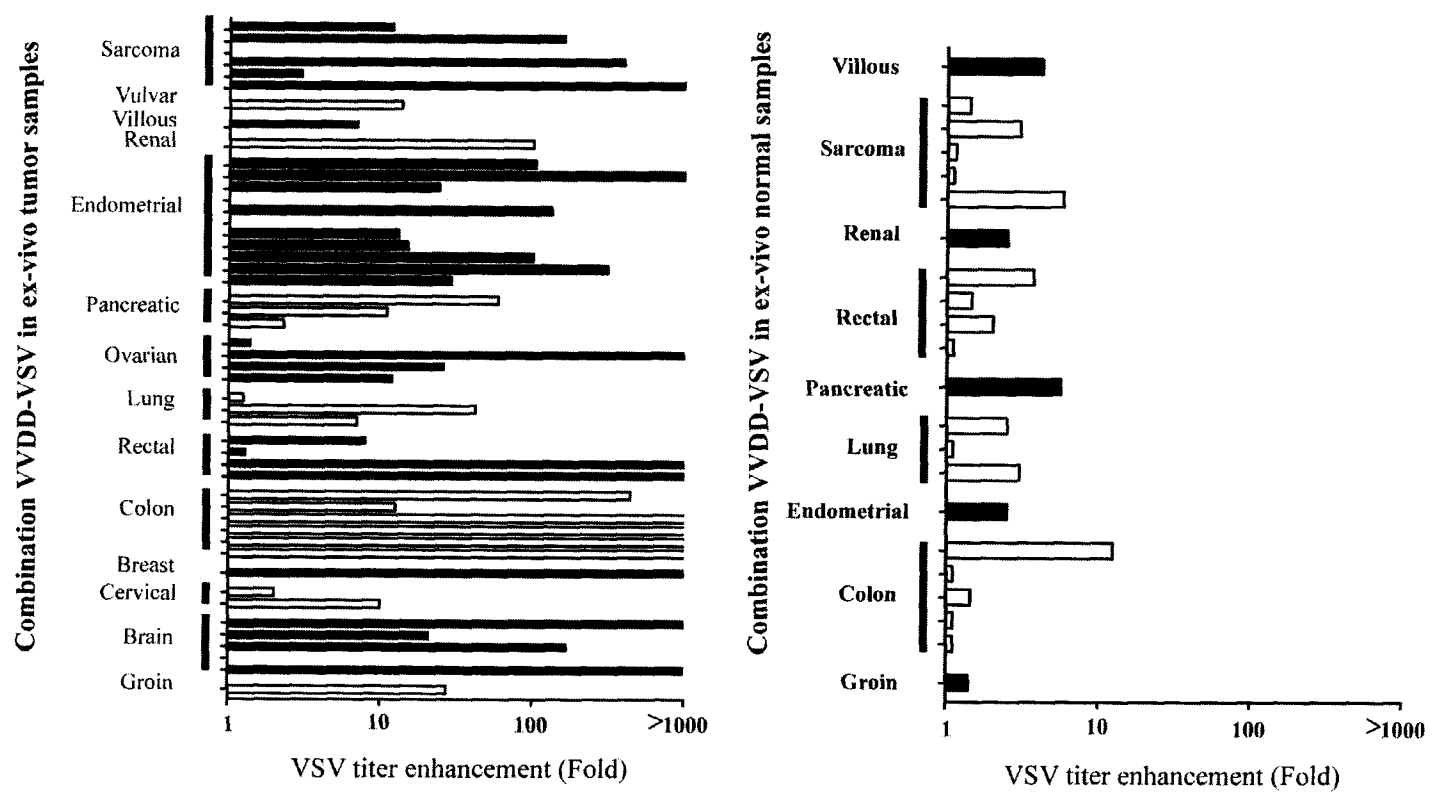

FIG. 4: Vaccinia virus enhances vesicular stomatitis virus expression into human ex vivo tumour. Human ex vivo rectal cancer and normal tissue specimens, colon cancer metastases in liver and normal liver, brain and endometrial cancer tissues were inoculated with $1 \times 10^8$ pfu of VVDD-eGFP for 2 hours in combination or not with VSVΔ51-DsRed for the last 45 minutes. Patient tumour specimens were homogenized in PBS, VSVΔ51 virus titers were determined using standard plaque assay on Vero cells to quantify viral replication. Each line corresponds to one patient. Black and white bars correspond respectively to the fold enhancement of VSVΔ51 in doubly with VVDD (44 patients) and VVΔB18R (30 patients) compared to singly infected cultures. Combination VV/VSVΔ51 samples were infected 2 hours by VVDD (1.10e7 pfu) and/or with VSVΔ51 (1.10e8 pfu) for the last 45 minutes. Samples were homogenized 48 hours after inoculation and processed for VSV titration.

FIG. 5: Model depicting how vaccinia virus with his B18R gene product protects the VSVΔ51 spreading. 75% confluent 786-O renal cancer cells were left untreated or treated with VVDD-eGFP (0.1 MOI) for 2 hours and VSV-FAST-DsRed (0.1 MOI) infection was then performed or not for 45 minutes. (A) VVDD and VSVFAST titers were determined 48 hours after infection. Mean±SEM from 3 independent working embodiments are presented. (B) Isobologram analysis: 786-0 cells were treated with serial dilutions of VVDD followed by VSVFAST (fixed ratio of 1:100 PFU) in 96-well plates and processed like in FIG. 1B, as described herein. CI: Combination indices. Fa: fraction of cells affected. Error bars represent the standard deviation of the estimate. One of two independent working embodiments in quadruplicate is presented. (C) 786-O cells were treated with of Vaccinia virus followed by VSV or VSVFAST. Cytotoxicity was assessed using MTS reagent after 72 hours. The Percentage of cell death was assessed. One of two independent working embodiments in duplicate is presented.

FIG. 6: Vaccinia virus enhances Semliki Forest Virus expression in vitro. 75% confluent 786-O renal cancer cells were left untreated or treated with VVDD-Cherry (0.1 MOI) for 2 hours and SFV-eGFP (0.1 MOI). Infection was then performed or not for 45 minutes. (A) VVDD and SFV titers were determined 48 hours after infection. Mean±SEM from 3 independent working embodiments are presented. (B) Isobologram analysis: 786-O cells were treated with serial dilutions of VVDD followed by SFV (fixed ratio of 100:1 PFU) in 96-well plates. Cytotoxicity was assessed using alamar blue reagent after 72 hours. Combination indices (CI) were calculated using Calcusyn software according to the method of Chou and Talalay. Plots represent the algebraic estimate of the CI in function of the fraction of cells affected (Fa). Error bars represent the standard deviation of the estimate. One of two independent working embodiments in quadruplicate is presented.

Figure 7A:
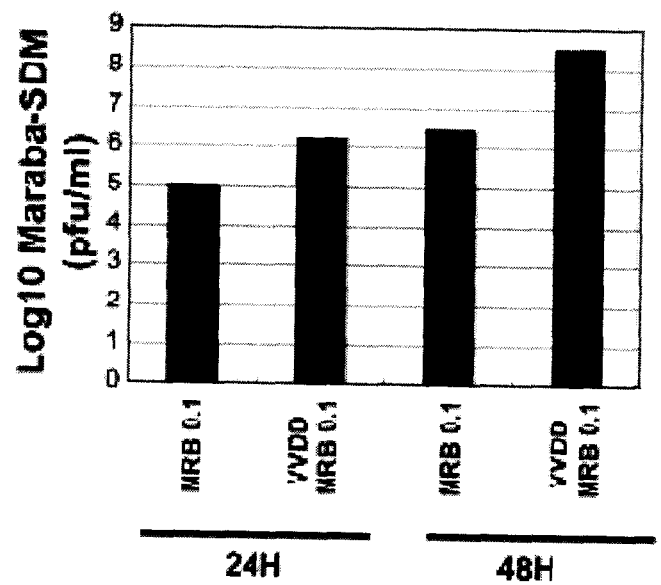
Figure 7B:
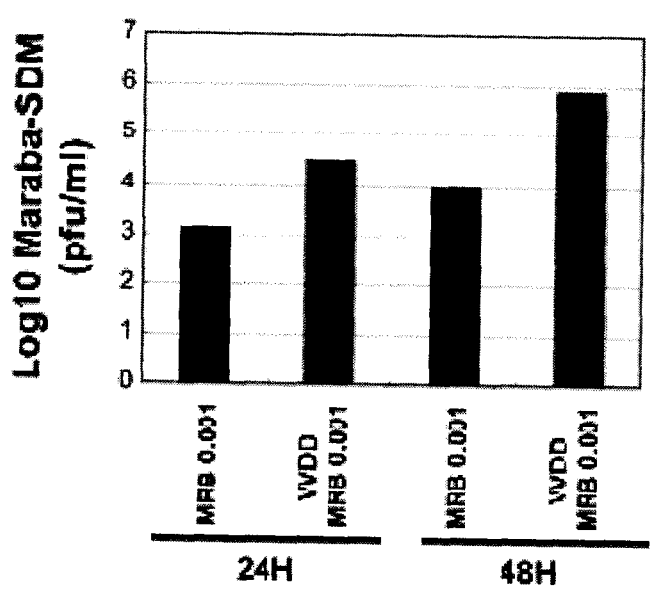

FIG. 7: VVDD enhances Maraba-SDM. 75% confluent colon cancer cells were left untreated or treated with VVDD-DsRed (0.1 MOI) for 2 hours and MRB-SDM-eGFP (0.1 or 0.001 MOI) infection was then performed or not for 45 minutes. Maraba-SDM titers were determined 24 and 48 hours after infection.

FIG. 8: VVDD enhances VSVΔ51FAST and VSVΔ51FAST enhances VVDD growth. 75% confluent 786-O renal cancer cells were left untreated or treated with VVDD-eGFP (0.1 MOI) for 2 hours and VSVFAST-DsRed (0.1 MOI) infection was then performed or not for 45 minutes. (A) VVDD and VSVFAST titers were determined 48 hours after infection. Mean±SEM from 3 independent working embodiments are presented. (B) Isobologram analysis: 786-O cells were treated with serial dilutions of VVDD followed by VSVFAST (fixed ratio of 1:100 PFU) in 96-well plates and processed as described herein. (C) The percentage of cell death was assessed. 786-O cells were treated with Vaccinia virus followed by VSV or VSVFAST. Cytotoxicity was assessed using MTS reagent after 72 hours.

DETAILED DESCRIPTION

Viruses may be categorized on the basis of their genetic material, as follows:
- ssRNA, positive sense viruses, such as the Picornaviridae, Caliciviridae, Togaviridae, Flaviviridae, and Coronaviridae;
- ssRNA, negative-sense viruses, such as the Rhabdoviridae, Filoviridae, Paramyxoviridae, and, Orthomyxoviridae;
- ssRNA, ambisense viruses, such as the Bunyaviridae, Arenaviridae;
- dsRNA, positive-sense viruses such as the Reoviridae, and Birnaviridae;
- ssRNA, DNA step in replication, such as the Retroviridae;
- ss/dsDNA, such as the Hepadnaviridae;
- ssDNA, such as the Parvoviridae; and,
- dsDNA, such as the Papovaviridae, Adenoviridae, Herpesviridae, Poxyiridae, and Iridoviridae.

In alternative embodiments, one or more strains of an oncolytic virus may be used in methods of the invention, simultaneously or successively. A virus may for example be selected from the group consisting of: adenovirus (a dsDNA Adenoviridae); reovirus (a dsRNA Reoviridae); herpes simplex virus (a dsDNA Herpesviridae), such as HSV1; Newcastle disease virus (a ssRNA Paramyxoviridae); vaccinia virus (a dsDNA Poxyiridae); Coxsackievirus (a ssRNA Picornaviridae); measles virus (a ssRNA Paramyxoviridae); vesicular stomatitis virus (VSV, a ssRNA Rhabdoviridae); influenza virus (a ssRNA Orthomyxoviridae); myxoma virus (a dsDNA Poxyiridae); Rhabdovirus (a ssRNA Rhabdoviridae), picornavirus (a ssRNA Picornaviridae).

Recombination between viral genomes is the formation of new, covalently linked combinations of genetic material from two different genomes. Recombination may be homologous or nonhomologous, and replicative or nonreplicative. These various mechanisms of recombination may require viral and/or host factors. In one aspect of the invention, oncolytic viruses are selected for contemporaneous use in a host, on the basis that recombination between the viral genomes in the host cells is minimized or precluded. In this sense, the viral genomes are "incompatible" for recombination in the host. In alternative embodiments, incompatible genomes may for example include:
- A viral DNA genome, whether double stranded (eg vaccinia, adenovirus, HSV) or single stranded (eg parvovirus) would be incompatible for recombination with a viral RNA genome (eg rhabdovirus, influenza, reovirus). The exception to this would be an RNA based virus that had a DNA replication intermediate form (eg a retrovirus);
- A positive sense RNA virus (eg. picorna virus) would be incompatible with a negative sense RNA virus (eg. rhabdovirus, measles, NDV);
- A double stranded RNA virus (eg. Reovirus) would be incompatible with a single stranded RNA virus (eg. Rhabdovirus).

In various aspects, the invention utilizes virulence factors. In the context of alternative embodiments, virulence factors may include a wide variety of virus-encoded proteins, the function of which is generally to modulate virus-host interactions, typically modulating cellular anti-viral responses (for example interfering with signals that trigger cell death by apoptosis) and as such often having activities analogous to cytokines or their receptors, adapted to modulate host immune responses. There is an extensive, and expanding, catalogue of virulence factors, available for use in alternative aspects of the invention. In some embodiments, virulence factors for use with the invention include secreted proteins, such as "virokines" or "viroceptors", being virally encoded proteins secreted from infected cells that can locally adapt the microenvironment for viral infection.

In some embodiments, virulence factors may be selected from virus-encoded proteins that modulate host responses, and in so doing typically have effects analogous to host cytokines (so that they may be called viral cytokines), possessing mainly immunosubversive activities.

Examples of such viral virulence factors include: 14.7 kDa orf virus protein, 16 kDa orf virus protein, 38K gene product of Cowpox virus, BCRF-1 of Epstein-Barr virus, CGF of Cowpox virus, CMV IL10 of cytomegalovirus, Herpesvirus glycoprotein D, HJ1 of cytomegalovirus, HVS13 of Herpesvirus saimiri, ICP34.5 of herpes simplex virus, MC148R of molluscum contagiosum virus, MGF of Myxoviruses, LMW23-NL of African swine fever virus, sis of simian sarcoma virus, orf virus IL10, Poxvirus growth factor, respiratory syncytial virus Glycoprotein G, SERP1 of Myxoma and Pox viruses, SERP2 of Myxoma virus, SFGF of Shope fibroma virus, tat protein of HIV, U83 of HHV-6, Vaccinia 19 kDa protein, viral IL6 of KSHV, viral IL8 of Marek's disease virus, viral IL17 of Herpesvirus saimiri, viral MIP-1-alpha of KSHV, viral MIP-2 of KSHV, viral MIP-3 of KSHV, VEGF-E of parapoxvirus Orf virus, or homologues or variants thereof, such as substantially identical sequences.

In alternative embodiments, virulence factions may also be selected from: B8R of vaccinia virus, B15R of vaccinia virus, B18R of vaccinia virus, BARF1 of Epstein-Barr virus, crmB of cowpox virus, crmC of cowpox virus, crmD of cowpox virus, crmE of cowpox virus, ECRF-3 of Herpesvirus saimiri, EHV-2 E1 ORF of Equine herpesvirus 2, G5R of Variola virus, GIF of orf virus, M3 of murine gammaherpesvirus 68, M11L of Myxoma virus, MC54L of molluscum contagiosum virus, M-T1 of Myxoma virus, M-T7 of Myxoma virus, ORF74 of Herpesvirus KSHV, p13 of ectromelia virus, Tanapoxvirus 38 kDa protein, T2 of Myxoma virus, U12 of human herpesvirus 6, U51 of human herpesvirus 6, US28 of Cytomegalovirus, vCCI of Vriola virus, vCKBP of Vaccinia virus, vIL18BP of vaccinia, ectromelia and cowpox virus, or homologues or variants thereof, such as substantially identical sequences.

In selected embodiments, the invention may involve the use of virulence factors that are virokines that locally increase cell proliferation, for instance the vaccinia encoded protein VGF which stimulates cell growth and leads to enhanced vaccinia infection. In a particular embodiment, a VGF coding sequence may be inserted into a VSV genome, for example in a first viral therapeutic to complement a VGF deleted vaccinia used as a second viral therapeutic.

In alternative embodiments, the virulence factor may be a virally encoded complement control protein (such as the vaccinia virus complement control protein VCP). Various complement control proteins have been characterized, and may be used in alternative embodiments, having a sequence homologous or identical to the following Genbank Accessions: CAM58194 [Vaccinia virus Ankara]; AAR17868 [Vaccinia virus]; CAE00483 [Ectromelia virus]; AAS49730 [Rabbitpox virus]; ABD97379 [Cowpox virus]; NP_570413 [Camelpox virus]; ABH08129 [Horsepox virus]; ABF22775 [Variola virus]; or CAE00480 [Ectromelia virus].

In alternative embodiments, the virulence factor may be a viral IL-17 (for example having a sequence homologous or identical to Genbank Accession Number CAA73627 [Saimiriine herpesvirus 2]).

In alternative embodiments, the virulence factor may be a Yaba like disease virus protein Y136 (Lee et al., Virology 281(2): 170-192 (2001); Huang et al., Proc Natl Acad Sci USA. 2007 Jun. 5; 104(23): 9822-9827; for example having a sequence homologous or identical to Genbank Accession Number NP_073521).

In alternative embodiments, the virulence factor may be a B8R protein, for example having a sequence homologous or identical to Genbank Accession Numbers: AAO89469 soluble interferon-gamma receptor-like protein [Vaccinia virus WR]; AAS49883 [Rabbitpox virus]; CAM58364 [Vaccinia virus Ankara]; ABH08298 [Horsepox virus]; AAF34077 [Vaccinia virus (strain Tian Tan)]; CAB96933 [Vaccinia virus (strain LIVP)]; AAA48205 [Vaccinia virus Copenhagen]; ABP88853 [Cowpox virus]; AAW67920 [Monkeypox virus]; AAL40628 [Monkeypox virus Zaire-96-I-16]; ABD97757 [Taterapox virus]; AAL73891 [Camelpox virus M-96]; ABF23752 [Variola virus]; CAE00470 [Ectromelia virus]; AAZ17459 [Skunkpox virus]; AAZ17461 [Raccoonpox virus]; AAZ17460 [Volepox virus]; YP_227387 [Deerpox virus W-848-83]; AAN02732 [lumpy skin disease virus]; NP_659582 [Sheeppox virus].

In alternative embodiments, the virulence factor may be a secreted protease, such as an MMP or trypsin.

In alternative embodiments, the virulence factor may be a Yaba Monkey Tumour Virus 2L protein (Rahman et al., J Biol Chem. 2006 Aug. 11; 281(32):22517-26; Brunetti et al., Proc Natl Acad Sci USA. 2003 Apr. 15; 100(8):4831-6; such as a protein having a sequence homologous or identical to Genbank Accession Numbers NP_938264 [Yaba monkey tumor virus]; ABQ43473 [Tanapox virus]; or CAC21240 [Yaba-like disease virus]).

In some embodiments, the virulence factor may be a membrane fusion protein, such as a reovirus Fusion Associated Small Transmembrane (FAST) protein sequence. WO 2002/044206 and WO 99/24582 describe a variety of FAST membrane fusion proteins, and functional motifs identified therein, derived from reovirus. In alternative embodiments of the invention involves, the membrane fusion proteins may have an amino acid sequence which is homologous to, or has a degree of identity to, at least regions the membrane fusion proteins encoded by Reoviridae, including functional fragments of those proteins (as for example disclosed by Top et al., PLoS Pathog. 2009 March; 5(3): e1000331), such as the Genbank amino acid sequences of four members of the FAST protein family, named according to their molecular masses: the p10 proteins of avian reovirus and Nelson Bay reovirus (Genbank Accession Numbers ABG43114 [Avian orthoreovirus]; ABA43652 [Muscovy duck reovirus]; ABY78878 [Psittacine orthoreovirus SRK/Germany/2007]; ABM67655 [Melaka orthoreovirus]; AAR13231 [Pulau reovirus]; ACC77635 [Kampar orthoreovirus]; ABW16998 [Reovirus strain HK23629/07]; and, AAF45157 [Nelson Bay reovirus]); the p14 protein of reptilian reovirus (Genbank Accession Number AAP03134) (SEQ ID NO: 1); and the p15 protein of baboon reovirus (Genbank Accession Number AAL01373), all functioning as promiscuous cellular fusogens. Other fusion proteins, that are distinct from the FAST sequences described above, include the fusogenic glycoprotein of gibbon ape leukemia virus (including sequences having substantially identical to the sequence of Genbank Accession Number AAC96083), the H and F membrane glycoproteins of measles virus (Horn et al., J Virol. 2005 February; 79(3):1911-7) and other members of the Paramyxovirus Family, and a variety of Herpes virus glycoprotein fusion proteins (Subramanian and Geraghty, Proc Natl Acad Sci USA. 2007 Feb. 20; 104(8):2903-8).

In some embodiments, the virulence factors may be selected so that a first virus expresses a virulence factor that inhibits the innate or adaptive immune response of the host, for example to locally prepare a tumour bed for infection by a second virus. In such an embodiment, the second virus may express an immune stimulating virulence factor that would enhance the host anti-tumour immune reaction. The two viruses in such an embodiment may for example be used sequentially, timed to allow the first oncolytic virus to spread, and then to recruit the immune system to a widespread oncolytic infection.

In some of the exemplified embodiments, the combination of vaccinia virus and VSVΔ51 enhances tumour infection and killing but does not significantly increase the infection of normal tissue. In fact, the combination treatment induced an increase of rhabdovirus VSVΔ51 spreading in various human tumour cell lines and subsequent cell death. The synergism between the two viruses was confirmed in a large panel of human tumour explants.

In various aspects of the invention, the vaccinia B18R gene product, a protein that is understood to be an early, soluble and surface antigen, may be used to bind IFNα/β/γ/ω with high affinity, and thereby mediate an attenuation of the interferon response of tumor cells. In selected embodiments, the B18R gene product may be used, for example by expression of the B18R gene in carrier cells used to transport an oncolytic virus, to improve the efficacy of oncolysis. Alternatively, a recombinant B18R gene may be introduced into a priming virus strain that would not normally express B18R. In this context, modifications of the B18R gene or gene product may be made, while retaining this activity. The invention accordingly provides recombinant carrier cells and priming viruses that encode proteins that are substantially identical to B18R.

The sequence of a vaccinia virusB18R protein is set out in Genbank Accession Number BAA00826 (Version BAA00826.1 G1:222699 (referencing Ueda et al., Virology 177 (2), 588-594 (1990); Goebel et al., Virology 179 (1), 247-266 (1990); and, Smith and Chan, J. Gen. Virol. 72 (PT 3), 511-518 (1991)) (SEQ ID NO: 2). Related soluble interferon-alpha/beta receptor sequences are for example disclosed in the following Genbank Accessions: AAX23631 [Rabbitpox virus]; AAX23632 [Buffalopox virus]; CAM58375 [Vaccinia virus Ankara]; AAF34090 [Vaccinia virus (strain Tian Tan)]; AAR91034 [Cantagalo virus]; AAA48218 [Vaccinia virus Copenhagen]; ABH08308 [Horsepox virus]; ABD97547 [Cowpox virus]; AAX23677 [Monkeypox virus]; AAL40635 [Monkeypox virus Zaire-96-1-16]; AAF74754 [BeAn 58058 virus]; YP_717517 [Taterapox virus]; ABF28175 [Variola virus]; AAA60926 [Variola major virus]; AAX23674 [Camelpox virus]; AAX23673; and CAC41986 [Ectromelia virus].

There are other interferon binding protein sequences known in the art, including viral sequences, with significant amino acid divergence from the vaccinia virus B18R sequence, including sequences that are the subject of the following Genbank Accessions: NP_659706 [Sheeppox virus]; AAL69871 [Swinepox virus]; AAN02861 [lumpy skin disease virus]; ABI99302 [Deerpox virus W-848-83]; NP_073521 [Yaba-like disease virus 136R protein]; ABQ43767 [Tanapox virus]; and, NP_051849 [Myxoma virus].

Alternative interferon binding proteins may be used in aspects of the invention, including engineered peptides. For example, US 2006/0286641 published on 21 Dec. 2006 describes polypeptides capable of binding interferon α and/or interferon β, and methods of rational protein design to arrive at such peptides. Related methods are for example disclosed in U.S. Pat. Nos. 7,083,950; 6,472,179; 6,475,983 and US Patent Publication 2003/0018174.

Definitions

A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be at least 10%, 20%, 30%, 40%, 50%, 52.5%, 55% or 60% or 75%, or more generally at least 80%, 85%, 90%, or 95%, or as much as 99% or 100% identical at the amino acid or nucleotide level to the sequence used for comparison using, for example, the Align Program (Myers and Miller, CABIOS, 1989, 4:11-17) or FASTA. For polypeptides, the length of comparison sequences may be at least 4, 5, 10, or 15 amino acids, or at least 20, 25, or 30 amino acids. In alternate embodiments, the length of comparison sequences may be at least 35, 40, or 50 amino acids, or over 60, 80, or 100 amino acids. For nucleic acid molecules, the length of comparison sequences may be at least 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, or as described herein). Examples of useful software include the programs Pile-up and PrettyBox. Such software matches similar sequences by assigning degrees of homology to various substitutions, deletions, insertions, and other modifications.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference.

The terms "nucleic acid" or "nucleic acid molecule" encompass both RNA (plus and minus strands) and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. One example of a modified RNA included within this term is phosphorothioate RNA. By "DNA" is meant a sequence of two or more covalently bonded, naturally occurring or modified deoxyribonucleotides. By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

An "isolated nucleic acid" is a nucleic acid molecule that is free of the nucleic acid molecules that normally flank it in the genome or that is free of the organism in which it is normally found. Therefore, an "isolated" gene or nucleic acid molecule is in some cases intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). In some cases, an isolated nucleic acid molecule is intended to mean the genome of an organism such as a virus. An isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstances, the material may be purified to essential homogeneity, for example as determined by PAGE or column chromatography such as HPLC. The term therefore includes, e.g., a genome; a recombinant nucleic acid incorporated into a vector, such as an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant nucleic acid which is part of a hybrid gene encoding additional polypeptide sequences. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector is included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded polypeptide, as probes for isolating homologous sequences (e.g., from other species), for gene mapping (e.g., by in situ hybridization with chromosomes), or for detecting expression of the nucleic acid molecule in tissue (e.g., human tissue, such as peripheral blood), such as by Northern blot analysis.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

As used herein, "heterologous" in reference to a nucleic acid or protein is a molecule that has been manipulated by human intervention so that it is located in a place other than the place in which it is naturally found. For example, a nucleic acid sequence from one species may be introduced into the genome of another species, or a nucleic acid sequence from one genomic locus may be moved to another genomic or extrachromasomal locus in the same species. A heterologous protein includes, for example, a protein expressed from a heterologous coding sequence or a protein expressed from a recombinant gene in a cell that would not naturally express the protein.

By "complementary" is meant that two nucleic acid molecules, e.g., DNA or RNA, contain a sufficient number of nucleotides that are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex.

Therapeutic Formulations

In various aspects, the invention provides compositions and methods for treating cancers, and related conditions such as treatment of benign, inoperable mass. For example the invention may involve the treatment of cancers characterized by the presence of solid tumours, including both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects, methods and compositions of the invention may also be useful in treating solid tumors arising from hematopoietic malignancies such as leukemias (i.e. chloromas, plasmacytomas and the plaques and tumors of mycosis fungoides and cutaneous T-cell lymphoma/leukemia) and lymphomas (both Hodgkin's and non-Hodgkin's lymphomas). In addition, aspects of the invention may be useful in the prevention of metastases from the tumors described above either when used alone or in combination with additional therapeutic approaches, such as radiotherapy or chemotherapy.

In one aspect, the invention involves administration (including co-administration) of therapeutic compounds or compositions, such as an oncolytic virus or agents that are effective to increase the susceptibility of a tumor cell to oncolytic viral infection in a host. In various embodiments, such agents may be used therapeutically in formulations or medicaments. Accordingly, the invention provides therapeutic compositions comprising active agents, including agents that are effective to increase the susceptibility of a tumor cell to oncolytic viral infection in a host, and pharmacologically acceptable excipients or carriers.

An effective amount of an agent of the invention will generally be a therapeutically effective amount. A "therapeutically effective amount" generally refers to an amount effective, at dosages and for periods of time necessary, to achieve the desired therapeutic result, such as increasing the susceptibility of a tumor cell to oncolytic viral infection in a host. A therapeutically effective amount a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

In particular embodiments, a preferred range for therapeutically effective amounts may vary with the nature and/or severity of the patient's condition. It is to be further understood that for any particular subject, specific dosage regimens should be adjusted over time according to the individual need and the professional judgement of the person administering or supervising the administration of the compositions.

A "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, active agents of the invention may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with another aspect of the invention, therapeutic agents of the present invention, such as agents that are effective to increase the susceptibility of a tumor or cancer cell to oncolytic viral infection in a host, may be provided in containers or kits having labels that provide instructions for use of agents of the invention, such as instructions for use in treating cancers.

Use of the present invention to treat or prevent a disease condition as disclosed herein, including prevention of further disease progression, may be conducted in subjects diagnosed or otherwise determined to be afflicted or at risk of developing the condition. In some embodiments, for oncolytic therapy, patients may be characterized as having adequate bone marrow function (for example defined as a peripheral absolute granulocyte count of >2,000/mm$^3$ and a platelet count of 100,000/mm$^3$), adequate liver function (for example, bilirubin<1.5 mg/dl) and adequate renal function (for example, creatinine<1.5 mg/dl).

Routes of administration for agents of the invention may vary, and may for example include intradermal, transdermal, parenteral, intravenous, intramuscular, intranasal, subcutaneous, regional, percutaneous, intratracheal, intraperitoneal, intraarterial, intravesical, intratumoral, inhalation, perfusion, lavage, direct injection, and oral administration and formulation.

Intratumoral injection, or injection into the tumor vasculature is contemplated for discrete, solid, accessible tumors. Local, regional or systemic administration also may be appropriate. For tumors of >4 cm, the volume to be administered may for example be about 4 to 10 ml, while for tumors of <4 cm, a volume of about 1 to 3 ml may be used. Multiple injections may be delivered as single dose, for example in about 0.1 to about 0.5 ml volumes. Viral particles may be administered in multiple injections to a tumor, for example spaced at approximately 1 cm intervals.

Methods of the present invention may be used preoperatively, for example to render an inoperable tumor subject to resection. Alternatively, the present invention may be used at the time of surgery, and/or thereafter, to treat residual or metastatic disease. For example, a resected tumor bed may be injected or perfused with a formulation comprising an oncolytic virus. The perfusion may for example be continued post-resection, for example, by leaving a catheter implanted at the site of the surgery. Periodic post-surgical treatment may also be useful.

In alternative embodiments, the invention may involve administering to a host a chemotherapeutic agent to augment killing of tumour cells during the secondary neutrophil response, such as chemotherapeutic agents that preferentially kills hypoxic tumour tissues. In alternative embodiments, the chemotherapeutic agent may for example be one or more of the following: dihydropyrimido-quinoxalines and dihydropyrimido-pyridopyrazines; quinoxaline or pyridopyrazine derivatives; 1,2-dihydro-8-piperazinyl-4-phenylimidazopyridopyrazine oxides and 1,2-dihydro-8-piperazinyl-4-phenylimidazo quinoxaline oxides; nitrophenyl mustard and nitrophenylaziridine alcohols, and their corresponding phosphates; anthraquinone compounds (as disclosed in WO 2005/061453); ligands based on alkylene amine oxime particularly butylene amine oxime ring structures, and radiometal complexes thereof (as disclosed in WO 1995/004552); 1,2,4 benzotriazine 1,4 dioxide compounds (WO 2005/082867); or nitro-substituted aromatic or hetero-aromatic compounds (EP 319329).

Continuous administration of agents of the invention may be applied, where appropriate, for example, where a tumor is excised and the tumor bed is treated to eliminate residual, microscopic disease. Continuous perfusion may for example take place for a period from about 1 to 2 hours, to about 2 to 6 hours, to about 6 to 12 hours, to about 12 to 24 hours, to about 1 to 2 days, to about 1 to 2 weeks or longer following the initiation of treatment. Generally, the dose of the therapeutic agent via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatments of the invention may include various "unit doses." A unit dose is defined as containing a predetermined-quantity of the therapeutic composition. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one may deliver 1 to 100, 10 to 50, 100 to 1000, or up to about $10^4$, $10^5$, $10^6$, $10^7$, $10^8$, $10^9$, $10^{10}$, $10^{11}$, $10^{12}$, $10^{13}$, $10^{14}$, or $10^{15}$ or higher infectious viral particles (vp) to the patient or to the patient's cells.

EXAMPLES

Compounds.

IFNα treatment was performed using Intron A (Shering), stored at 4° C. at stock concentration $10 \times 10^6$ IU/ml. The recombinant B18R protein (Vaccinia Virus-Encoded Neutralizing Type I IFN Receptor) was purchased from eBioscience, stored at −80° C. at 0.1 mg/ml.

Cell Lines.

Human HT29 colon carcinoma, human SKOV3 ovarian carcinoma, human 786-0 renal carcinoma (American Type Tissue Collection), human U2OS osteosarcoma cells and the African Green Monkey Vero kidney epithelial cells were purchased from American Type Culture Collection and propagated in HyQ Dulbecco's modified Eagle medium (High glucose) (HyClone) supplemented with 10% fetal calf serum (CanSera, Etobicoke, Canada).

Viruses. Vaccinia Viruses:

The 818R deleted strain of WR and the cloning plasmid pSC65-Firefly luciferase were kindly provided by Dr Steve Thorne (Department of Pediatrics and Bio-X Program, Stanford University, Stanford, Calif., United States of America). The VVDD-enhancedGFP (VVDD-eGFP), vaccinia virus double deleted for VGF (Vaccinia Growth Factor) and thymidine kinase (TK) genes, and the pSEL-eGFP plasmid were provided by Dr Andrea McCart (Division of Experimental Therapeutics, Toronto General Research Institute, Toronto, Ontario, Canada). Vaccinia ΔB18R-eGFP (VVΔB18R-eGFP) was made by insertion of eGFP-DNA into the vaccinia thymidine kinase (TK) gene by homologous recombination. Successful recombinants were selected by eGFP expression and plaque-purified. All vaccinia viruses were propagated in U2OS cells. Infected U2OS cells were harvested, resuspended in 1 mM Tris pH 9.0, and virions were purified following freeze-thaw cell lysis and centrifugation at 11500 rpm on a 36% sucrose cushion. Viral pellets were resuspended in 1 mM Tris pH 9 for all animal studies. VSV viruses: The recombinant AV3 strain of VSV with an attenuating deletion of methionine 51 of the matrix protein and a transgene encoding RFP (VSVΔ51-DsRed), or enhanced GFP-luciferase (VSVΔ51-Luc) were propagated in Vero cells (Power et al., 2007). Virions were purified from cell culture supernatants by passage through a 0.2 μm Steritop filter (Millipore, Billerica, Mass.) and centrifugation at 11500 rpm before resuspension in phosphate-buffered saline (PBS) (Hyclone, Logan, Utah) for all animal studies. The recombinant VSVΔ51 with transgenes encoding FAST protein and RFP (VSVFAST-DsRed) were propagated in Vero cells (Brown et al., 2009). SFV virus: The construction of replication-competent SFV vector VA7-EGFP has been described (Vaha-Koskela et al., 2003).

Isobologram Analysis on HT29 and 786-0 Cells.

HT29 or 786-0 cells were respectively plated at 100000 and 50 000 cells per well in a 96-well plate and allowed to adhere overnight. The next day serial dilutions of VVDD and VSVΔ51 or SFV were added keeping a respectively constant ratio of 100 to 1 for 786-0 cells. Alamar blue reagent was used to assess cellular metabolic activity following 72 h incubation with drug and/or virus. Calcusyn was used to compute the CI where CI<0.7 is considered synergistic (Chou, 2006). CI Error bars represent the standard deviation estimate.

Mice and Tumour Models.

All mice used were obtained from Charles River Laboratories. Imaging Studies: Human xenograft colon carcinoma HT29 tumours were established subcutaneously in 6 weeks old CD1 female nude mice (n=4) by injecting $3 \times 10^6$ cells suspended in 100 μl PBS. Palpable tumours formed within approximately 10 days after seeding. VVDD-eGFP was administered intravenously at $1 \times 10^6$ pfu/mouse. VSV-Luc ($1 \times 10^7$ pfu) was administered intravenously 2 to 3 days after vaccinia virus treatment. Efficacy Studies: For the subcutaneous HT29 xenograft model, mice were treated X times with X virus doses/combinations, and tumours were measured every 3-4 days using an electronic caliper. Tumour volume was calculated as $(L_1)^2 * L_2 / 2$.

In Vivo Imaging.

Mice were injected with d-luciferin (Molecular Imaging Products Company, Ann Arbor, Mich.) (200 μl intraperitoneally at 10 mg/ml in PBS) for firefly luciferase imaging. Mice were anesthetized under 3% isofluorane (Baxter Corp., Deerfield, Ill.) and imaged with the in vivo imaging system 200 Series Imaging System (Xenogen Corporation, Hopkinton, Mass.). Data acquisition and analysis was performed using Living Image v2.5 software. For each embodiment, images were captured under identical exposure, aperture and pixel binning settings, and bioluminescence is plotted on identical colour scales.

Immunohistochemistry (IHC).

Tissues were harvested, placed in OCT mounting media (Tissue-Tek, Sakura Finetek, Torrance, Calif., USA) and cut in 5 μm sections with a microtome cryostat (Microm HM500 OM Cryostat). Sectioned tissues were fixed in 4% paraformaldehyde for 20 minutes and used for hematoxylin and eosin (H&E) staining or immunochemistry (IHC). IHC was performed using a Vecastain ABC kit for rabbit primary antibodies (Vector Labs, Burlingame, Calif.), according to manufacturer's instructions. Primary antibodies used were rabbit polyclonal antibodies against VSV (gift of Earl Brown) and active caspase 3 (BD Pharmingen, Rockville, Md.). Briefly, endogenous peroxidase activity was inhibited by incubating with 3% $H_2O_2$ followed by blocking of non-specific epitopes with 1.5% normal goat serum. Subsequently, all sections were incubated with avidin then biotin blocking agents, each for a period of 15 min. PBS washes were performed between all blocking and incubating steps. Sections were then incubated with primary antibodies, either anti-VSV antibody (1:5000, 30 minutes), anti-active caspase 3 antibody (1:200, 60 minutes), followed by anti-rabbit biotinylated secondary antibody. The avidin: biotinylated enzyme complex obtained from the ABC Vectastain Kit was added to each slide for 30 min. After three consecutive PBS washes, the antigen was localized by incubation with 3,3-diaminobenzidine reagent. Sections were counterstained with hematoxylin. For assessment of cell morphology, sections were stained with hematoxylin and eosin according to standard protocols. Whole tumour images were obtained with an Epson Perfection 2450 Photo Scanner while magnifications were captured using a Zeiss Axiocam HRM Inverted fluorescent microscope and analyzed using Axiovision 4.0 software.

Explant Preparation, Culture, Infection and Titration.

Primary cancer and normal (when available) tissues specimens were obtained from consenting patients who underwent tumour resection. All tissue specimens were processed within 48 hrs post surgical excision. Samples were manually divided using a 15 mm scalpel blade into approximately 10-mm$^3$ pieces and placed on 12 wells plate with alpha medium containing 10% fetal bovine serum under sterile techniques. VVΔB18R and VVDD both encoding enhanced green fluorescent protein (eGFP) were then added directly to the specimen (10$^7$ PFU) and allowed to infect for 2 hours at 37° C. In the last 45 min, VSVΔ51 encoding DsRed was also added to the specimen (10$^8$ PFU) before covering specimens with medium containing serum. At 48 hours, specimens were visualized using fluorescence microscopy. After the indicated treatment condition, samples were weighed and homogenized in 0.5 ml of PBS using a homogenizer (Kinematica AG-PCU-11). Serial dilutions of tissue preparations were prepared in serum free media and viral titers were quantified by standard plaque assay.

VSV and VV Titration from In Vitro Cancer Cells, In Vivo Tumour and Ex Vivo Patient Tissue Samples.

Supernatants from each treatment condition were collected at the specified time point. A serial dilution was then performed in DMEM and 200 µl of each dilution was applied to a confluent monolayer of Vero cells for 45 minutes. Subsequently, the plates were overlayed with 0.5% agarose in DMEM-10% FBS and the plaques were grown for 24 h. Cornoy fixative (Methanol:Acetic Acid is 3:1) was then applied directly on top of the overlay for 5 minutes. The overlay was gently lifted off using a spatula and the fixed monolayer was stained via 0.5% crystal violet for 5 minutes, after which the plaques were counted. VVDD samples were titered on U2OS monolayer using 1.5% carboxyl methyl cellulose in DMEM-10% FBS for 48 h. The overlay was removed and the monolayer stained via 0.5% crystal violet for 5 minutes, after which the plaques were counted. In vivo tumours were homogenized into 500 µl PBS and processed as described for in vitro studies.

Statistics.

In vivo data regarding virus titration of tumour. For those studies, mice were randomly assigned to the treatment groups 5 mice for PBS, 9 mice for VVDD/VSV and 5 mice for VVDB18R/VSV. A T-test statistic was done comparing group VVDD/VSV to VVDB18R/VSV. $P<0.005$ was considered statistically significant. Ex vivo data regarding virus titration of human samples. A pair T. Test statistics was done comparing VVDD/VSV fold enhancement to VVDB18R/VSV fold enhancement human samples. Only samples that were tested for both VVDD/VSV and VVΔB18R/VSV were included for the statistic test. $P<0.05$ was considered statistically significant.

Example 1: Vaccinia Virus Enhances Vesicular Stomatitis Virus Infection In Vitro The wild type strain of VSV expresses a protein (the M or matrix protein) that upon infection, acts as an intracellular antagonist of IFN production by blocking the transport of IFN mRNAs from the nucleus. In earlier studies it was determined that a variant of the virus (VSVΔ51) with an engineered mutation in the M protein is unable to block the expression of IFN genes following virus infection and thus has restricted growth in normal cells that have an intact anti-viral response. VSVΔ51 grows to levels comparable to wild type virus in a broad spectrum of cancer cells that lack either the ability to produce or respond to IFN. However, it was determined that some human tumour cell lines HT29 (colon), SKOV-3 (ovary) and 786-0 (kidney) retain at least partial responsiveness to IFN and only poorly support the spread of VSVΔ51 as described in FIG. 1 and as determined by fluorescent detection under the following conditions: 75% confluent HT29 colon, 786-0 renal or SKOV-3 ovarian cancer cells were left untreated or treated with VVDD-eGFP (0.1 MOI) for 2 hours, or with VSVΔ51-DsRed (0.0001 MOI HT29 and SKOV-3 or 0.1 786-O) for 45 minutes, or in combination with the two viruses, VVDD for 2 hours and 4 hours later with VSVΔ51 during 45 minutes. eGFP (VV) and DsRed (VSV) fluorescence were detected 48 hours after VSVΔ51 infection. 72 hours following VSVΔ51 infection, viral oncolytic effect was assessed by a crystal violet assay demonstrating massive cell death in double-treated conditions.

It was confirmed, however, that these VSVΔ51 resistant cell lines can be productively infected by an oncolytic version of vaccinia described herein and referred to as VVDD. Following infection, VVDD expresses a gene product, B18R that binds to and locally sequesters the anti-viral cytokines IFNα/β. Tagged versions of VVDD (eGFP) and VSVΔ51 (RFP) were created that allowed for the monitoring of each of the viruses to spread within a co-infected culture.

Figure 1B:
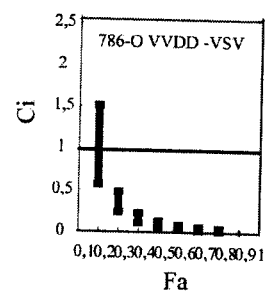

The HT29 cells supported VVDD infection although at low multiplicities of infection, (MOI 0.1 pfu/cell) 48 hours was insufficient time for VVDD to spread throughout the monolayer (as measured by GFP expression) or complete killing of the culture. If VVDD infection was followed by a thousand times lower dose of VSVΔ51, we observed both a rapid spread of VSV and complete killing of the HT29 cell culture. This was true of the SKOV-3 and 786-0 tumour cell lines as well. These embodiments demonstrate the ability of VVDD to initiate infection of a cancer cell line and create a local environment that sensitizes a previously resistant culture to the rapid oncolytic effects of VSV. As expected the accelerated spread of VSVΔ51 correlated with a thousand fold increase in virus production compared to singly infected cultures as shown in FIG. 1A. Isobologram analysis revealed that coinfection with the two viruses resulted in synergistic killing of the cancer cell lines as shown in FIG. 1B. Examination under fluorescence microscope revealed that, in general, the RFP and GFP images did not overlap, suggesting that increased oncolysis was not due to enhanced uptake of VSV in VV-infected cells but rather due to sensitization of neighbouring cells to VSVΔ51 infection. To exclude that the observed VV-driven enhancement was not restricted to VSV, another IFN-sensitive RNA virus, Semliki Forest virus (SFV) as challenge. Results with SFV were very similar to those with VSVΔ51, suggesting that vaccinia virus may have a universal capacity to facilitate spread of IFN-sensitive viruses, as described herein and in FIG. 6.

Example 2: The VV B18R Gene Product Enhances VSV Replication in HT29 Cancer Cell Lines In Vitro IFN responsiveness of HT29 colon cancer cells was examined. 75% confluent HT29 colon cancer cells were pretreated or not with IFN α (IntronA at 30 IU) for 17 hours.

Then, cells were left untreated or treated with VVDD-eGFP (0.1 MOI) for 2 hours, or with VSVΔ51-DsRed (0.0001 MOI) for 45 minutes alone or in the combination, VVDD for 2 hours and VSVΔ51 for the last 45 minutes. eGFP (VV) and DsRed (VSV) fluorescence were detected 48 hours after VSVΔ51 infection. Pictures showed that VSVΔ51 alone poorly replicate in these cells. On the contrary, in combination with VVDD, VSVΔ51 replicate in HT29. In comparison, with IFN α pre-treatment, even if VVDD can infect and spread, VSVΔ51 was not enhanced. In another embodiment, 75% confluent HT29 colon cancer cells were pre-treated or not with various concentration of recombinant B18R protein (10e-1 to 10e-6 μg). DsRed (VSV) fluorescence was detected 48 hours after VSVΔ51 infection. HT29 cells were protected from infection by VSVΔ51 but retained some susceptibility to vaccinia infection at the concentration of IFN used.

Also examined was whether a factor secreted by VVDD infected cells was responsible for the sensitization of HT29 cells to VSVΔ51 infection. 75% confluent HT29 colon cancer cells were left untreated or treated with VVDD-eGFP or VVΔB18R-eGFP (0.1 MOI) for 2 hours. Supernatant of each condition was filtered using a 0.22 μm filter (that blocks vaccinia viruses), and the filtrated media was added to naïve HT29 cells. Supernatants from VVDD infected cultures were collected 24 hours post infection, filtered (to remove VVDD) and applied to naïve cultures of HT29 cells. These cultures were subsequently infected (or not) with VSVΔ51-DsRed (0.0001 MOI) infection was then performed or not for 45 minutes. eGFP (to verify the effective blockage of VVDD) and DsRed (VSV) fluorescence HT29 were detected 48 hours after VSVΔ51 infection. Under conditions described herein, a factor(s) present in the supernatants of VVDD infected cultures was sufficient to sensitize HT29 cells to infection by VSV.

To determine if the B18R protein was at least partially responsible for the enhancement of VSVΔ51, a recombinant VV strain was developed which lacked the B18R gene (VVΔB18R-eGFP). 75% confluent HT29 colon cancer cells were left untreated or treated with VVDD-eGFP or VVΔB18R-eGFP (0.1 MOI) for 2 hours alone, in combination with VSVΔ51-DsRed (0.0001 MOI) or not for 45 minutes. eGFP and DsRed fluorescence respectively from VVs and VSVΔ51 infection were detected 48 hours after VSVΔ51 infection. In sum, infection of HT29 cells by VSVΔ51 was greatly enhanced by VVDD but much less so by the VVΔB18R virus. This enhancement was reflected in the amounts of VSV□51 produced from co-infected cultures (FIG. 2B) with 100 times more VSVΔ51 produced in VVDD co-infected cultures than in VVΔB18R co-infections. As described in FIG. 2B, VSV titers were determined after infection of HT29 cells with VSVΔ51 at 0.0001 MOI after 48 hours. Supernatants were collected for standard plaque assay as described in FIG. 2A.

Figure 2A:
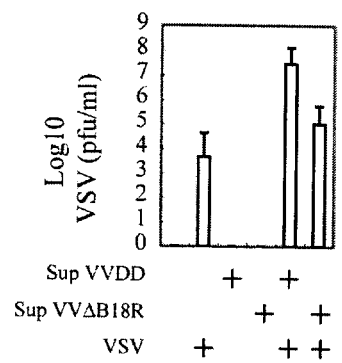
Figure 2B:
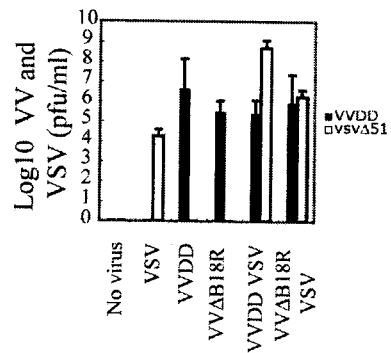
Figure 2C:
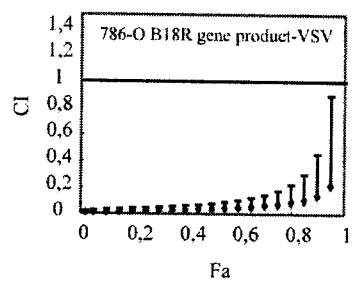

Filtered supernatants from VVΔB18R infected cultures were determined to be much less potent than supernatants from VVDD infected cultures at promoting VSVΔ51 spread and virus production in HT29 cells. Isobologram analysis was performed as described herein. Briefly, 786-0 cells were treated with serial dilutions of B18R gene product followed by VSV (fixed ratio of 1 μg:50000 PFU) in 96-well plates and processed like in FIG. 1D. The results for these embodiments are shown in FIG. 2C.

In a further embodiment, 75% confluent HT29 colon cancer cells were pre-treated or not with IFNα (30 IU) and treated or not with VVDD or VVΔB18R-eGFP (0.1 MOI) for 2 hours during two hours. In the last 45 minutes, VSVΔ51-DsRed (0.0001 MOI) was added in combination or not with recombinant B18R protein (10e-2 μg) eGFP (VV) and DsRed (VSV) fluorescence were detected 48H00 after VSVΔ51 infection.

In a further embodiment, HT29 colon cancer cells were pre-treated or not with various concentration of recombinant B18R (10e-1 to 10e-6 μg) protein during 2 hours or, cells were treated with VVDD-eGFP or VVΔB18R-eGFP (0.1 MOI) for 2 hours. Then, VSVΔ51-DsRed (0.0001 MOI) was added with or not various concentration of INFα (5 to 30 IU). Supernatants were collected for standard VSVΔ51 plaque assay 48 hours later.

Figure 2D:
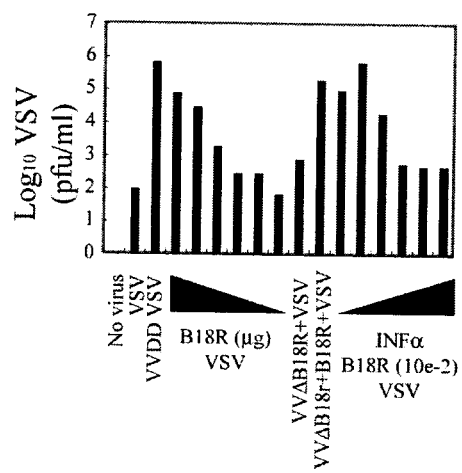
Figure 3B:
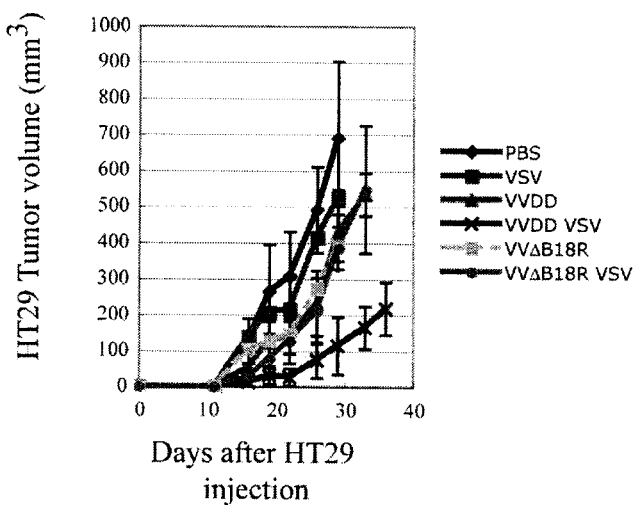
Figure 3C:
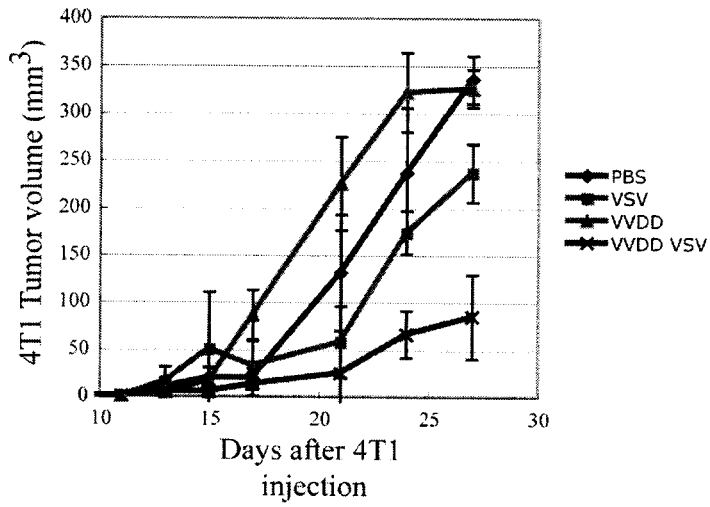

As detailed herein, purified recombinant B18R protein when added to HT29 cultures directly was able to support, in a dose dependent fashion, robust growth and spread of VSVΔ51, as shown in FIG. 2D, as well as complement the VVΔB18R virus in enhancing VSV□51 infection of HT 29 cells. The activity of B18R protein could be overcome by supplementing cultures with exogenous IFN alpha (INFα). This demonstrates that the spread of VSVΔ51 is restricted by the relative ratios of B18R and INFα suggesting that in vivo, the growth of VSVΔ51 will be limited by the relative concentration of B18R in the tumour microenvironment.

Example 3: Vaccinia Virus Enhances VSVΔ51 Replication Specifically in Tumour Beds HT29 subcutaneous xenograft tumour models were established in nude mice. After tumour growth, group received VVDD-eGFP (1.10e6 pfu) and 2 days after, VSVΔ51-Luciferease (1.10e7 pfu) was also injected intravenously. Viral replication at tumour site was imaged using IVIS imaging system at day 3, 7 and 9 after VSVΔ51 injection for GFP and Luciferase. 3 days after infusion, VVDD gene expression was restricted to sites of human tumour growth. Tumour mice corresponding to combination treatments, showed a strong signal of VSVΔ51 after 5 days until day 9. At this time, VSVΔ51-Luciferase was administered intravenously and the expression of the virally encoded reporter monitored over time. VSVΔ51-associated luciferase expression was observed in tumours only in doubly infected animals. The VSVΔ51-luciferase signal peaked at approximately 7 days post infection but remained detectable by IVIS imaging in the tumour for up to 11 days post-infection.

Further, nude mice were injected by intravenous with VVDD-eGFP (1.10e6 pfu/mice). GFP associated expression was controlled by microscope 2 days after intravenous injection in live mice. At days 11 after VSVΔ51 injection, mice were sacrificed. Tumours were removed by surgery and placed on a plate to verify the specific expression of VSVΔ51 into the tumour. Combination treatment tumour mice shown more abundant presence of VSVΔ51.

VVDD and VVΔB18R viruses were compared and contrasted for their ability to promote VSV replication in tumour bearing mice as shown in FIG. 3A. While both viruses could enhance VSVΔ51 replication specifically in tumours, their relative potency in this respect mirrored our in vitro studies described above. Indeed when VVΔB18R/VSVΔ51 co-infected tumours were harvested, homogenized and analyzed for virus titres by plaque assay, we found 1000 times more VSVΔ51 in VVDD infected tumours than in VVΔB18R infected tumours (FIG. 3A).

The presence and disposition of VSV in human tumours was determined by immunohistochemical staining with anti-VSV antibodies. While tumours infected only with VSV had little or no detectable viral proteins, as expected there was evidence of widespread VSV infection in co-infected tumours. Infection of tumours with VSV leads to widespread induction of apoptosis as revealed by immunohistochemical detection of active caspase 3. Enhanced replication of VSV in dually infected tumours was observed in the case of both, human xenograft and immune competent mouse breast tumour models (FIGS. 3B and 3C).

At the treatment doses used in these embodiments, it was found that therapy with either virus on its own had little impact on these rapidly growing tumours. However when VVDD and VSV were sequentially administered, tumour growth was slowed significantly.

During the course of monitoring, virus replication even in co-infected animals was restricted to tumour beds with no evidence of infection of normal tissues detected by imaging or immunohistochemical staining.

Example 4: Vaccinia Virus Enhances Vesicular Stromatitis Virus Expression in Human Tumour Tissues Ex Vivo The embodiments described above demonstrate synergistic interactions between vaccinia and VSV oncolytics in established tumour cell lines and animal models. This was tested in intact primary human biopsy samples.

Human tissue explants with specific pathologies, including both tumour and normal tissue (when available) were obtained from patients undergoing surgical resection. Tissue slices were prepared from each sample and then infected singly or in combination with oncolytic viruses. Briefly, human ex-vivo rectal cancer and normal tissue specimens, colon cancer metastases in liver and normal liver, brain and endometrial cancer tissues were inoculated with $1\times10^8$ pfu of VVDD-eGFP for 2 hours in combination or not with VSVΔ51-DsRed for the last 45 minutes. eGFP and DsRed expression was monitored by fluorescence microscopy 48 hours after viral inoculation.

In all embodiments uninfected slices were visualized by epifluorescence microscopy to determine the level of background fluorescence emanating from the tissue. Images of enhanced VSV infection in primary tumour samples in the presence of VVDD were viewed. For example, in one patient both rectal tumour tissue and adjacent normal tissue and consistent with the mouse models described herein, it was observed that oncolytic virus growth was only in tumour slices and not in adjacent normal tissue. Similar results were seen in a paired normal and tumour sample from a patient with metastatic colon cancer in the liver.

The fluorescent images provide a qualitative read-out but to confirm this phenomenon quantitatively, the amount of virus produced from the infected cultures was quantified as shown in FIG. 4. Patient tumour specimens were homogenized in PBS, VSVΔ51 virus titers were determined using standard plaque assay on Vero cells to quantify viral replication. As shown in FIG. 4, each line corresponds to one patient (Type of tumour # number of patient). Black and white bars correspond respectively to the fold enhancement of VSVΔ51 in doubly with VVDD (44 patients) and VVΔB18R (30 patients) compared to singly infected cultures. Combination VV/VSVΔ51 samples were infected 2 hours by VVDD (1.10e7 pfu) and/or with VSVΔ51 (1.10e8 pfu) for the last 45 minutes. Samples were homogenized 48 hours after inoculation and processed for VSV titration. Data were classified from the highest increase to the lowest one for VVDD/VSV combination.

For these studies, immediately following the adsorption of virus, separate samples were taken to provide a baseline for the remaining input virus. At 48 hours after infection, slices were homogenized and virus titres determined. The results presented in FIG. 4 are the fold enhancement of VSVΔ51 in doubly versus singly infected cultures in a wide range of malignancies. In 33 of 44 tumour samples we observed a ten to ten thousand fold increase in VSV titres following co-infection of tumour samples with vaccinia virus. In the majority of available adjacent normal samples no significant infection with VSVΔ51 in the presence of VVDD was observed.

Example 5: VSVΔ51 can be Engineered to Enhance VVDD Growth

VVDD can enhance VSVΔ51 growth by conditioning the tumour microenvironment to be non-responsive to antiviral cytokines like IFN. These embodiments illustrate a VSVΔ51 strain that could reciprocate and produce a virally encoded gene product that would enhance VVDD growth and/or spread. Approximately 90% of VVDD produced during an infection remains inside the infected cell throughout the virus growth cycle as discussed in (Moss and Earl, 2001 and Moss, 2006).

Figure 5A:
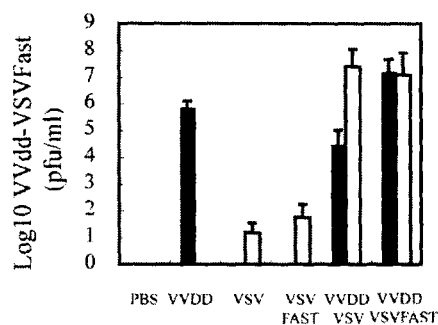
Figure 5B:
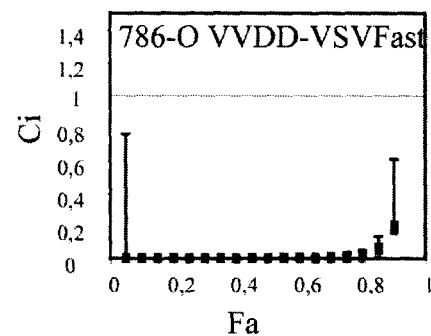
Figure 5C:
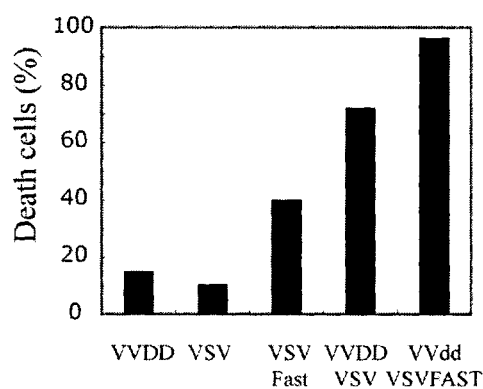

A VSVΔ51 recombinant was developed that expresses a fusion-associated small transmembrane (p14 FAST) protein that locally induces cell fusion. The p14 FAST protein is a small integral membrane protein originally isolated from a reptilian reovirus that spontaneously initiates cell membrane fusion. 75% confluent 786-O renal cancer cells were left untreated or treated with VVDD-eGFP (0.1 MOI) for 2 hours and VSVFAST-DsRed (0.1 MOI) infection was then performed or not for 45 minutes. eGFP (VV) and DsRed (VSVFAST) fluorescence were detected 48 hours by microscopy after VSVFAST infection. One of three independent embodiments is presented. VVDD and VSVFAST titers were determined 48 hours after infection as shown in FIG. 5A. As shown in FIG. 5B, an isobologram analysis was performed. Briefly, 786-0 cells were treated with serial dilutions of VVDD followed by VSVFAST (fixed ratio of 1:100 PFU) in 96-well plates and processed like in FIG. 1D. 72 hours following VSVFAST infection, viral oncolytic effect was assessed by a crystal violet assay demonstrating massive cell death in double-treated conditions. As shown in FIG. 5C, the percentage of cell death was assessed. 786-O cells were treated with of Vaccinia virus followed by VSV or VSVFAST. Cytotoxicity was assessed using MTS reagent after 72 hours. One of two independent working embodiments is presented. 75% confluent 786-O renal cancer cells were left untreated or treated with VVDD (0.1 MOI) for 2 hours and/or VSVFAST without any tag (0.1 MOI) for 45 minutes. eGFP (VV) fluorescence was detected 48 hours after SFV infection. Patient colon tumour specimen was infected by VVDD (eGFP) for 2 hours with 1.10e7 pfu and/or VSVFAST (DsRed) with 1.10e8 pfu for 45 minutes. eGFP and DsRed expression was monitored 48 hours after viral inoculation.

In in vitro and ex vivo co-infection embodiments, it was determined that that VVDD and VSVFAST interacted in a synergistic fashion (see FIG. 5B) with increased cell killing, virus spread of both viruses translating in over 100 fold increase in vaccinia virus production.

Example 6: Vaccinia Virus Enhances Semliki Forest Virus Expression In Vitro

75% confluent 786-O renal cancer cells were left untreated or treated with VVDD-Cherry (0.1 MOI) for 2 hours and SFV-eGFP (0.1 MOI). Infection was then performed or not for 45 minutes. eGFP (SFV) and Cherry (SFV) fluorescence were detected 48 hours after SFV infection.

Figure 6A:
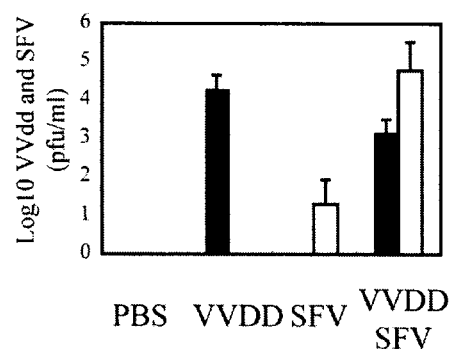
Figure 6B:
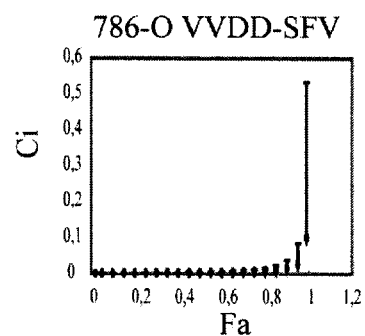

As shown in FIG. 6A, VVDD and SFV titers were determined 48 hours after infection. As shown in FIG. 6B, an isobologram analysis was conducted. Briefly, 786-O cells were treated with serial dilutions of VVDD followed by SFV (fixed ratio of 100:1 PFU) in 96-well plates. Cytotoxicity was assessed using alamar blue reagent after 72 hours. Combination indices (CI) were calculated using Calcusyn software according to the method of Chou and Talalay.

Example 7: VVDD Enhances Maraba-SDM

In this set of illustrative embodiments, 75% confluent CT26 colon cancer cells were left untreated or treated with VVDD-DsRed (0.1 MOI) for 2 hours and MRB-SDM-eGFP (0.1 or 0.001 MOI) infection was then performed or not for 45 minutes. DsRed (VV) and eGFP (MRB-SDM) fluorescence were detected at 48 hours by microscopy after Maraba infection. Maraba-SDM titers were determined 24 and 48 hours after infection as shown in FIG. 7.

Example 8: VVDD Enhances VSVΔ51FAST and VSVΔ51FAST Enhances VVDD Growth

Figure 8A:
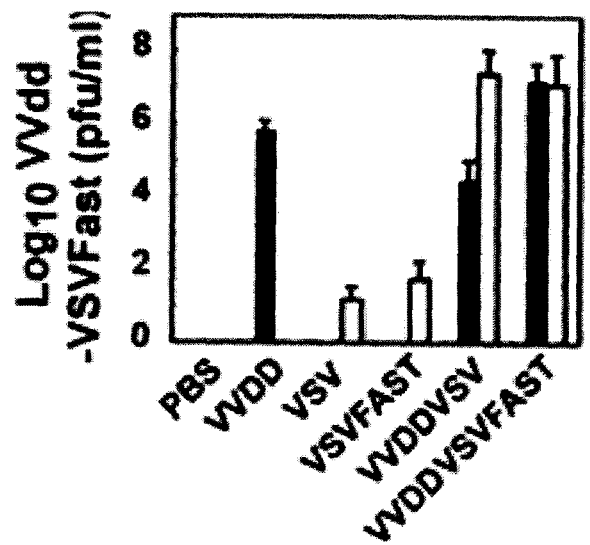
Figure 8B:
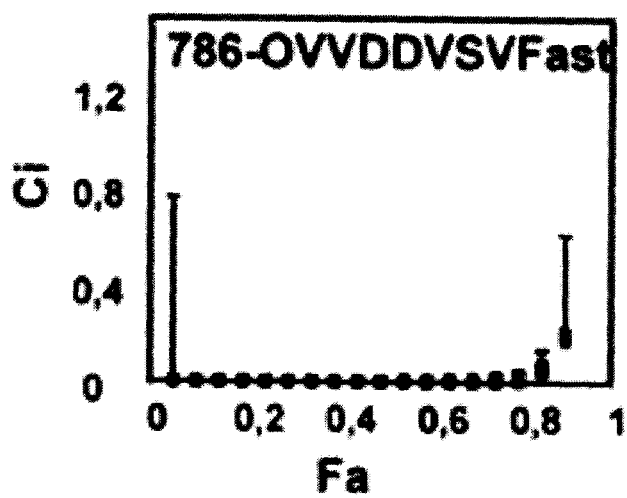
Figure 8C:
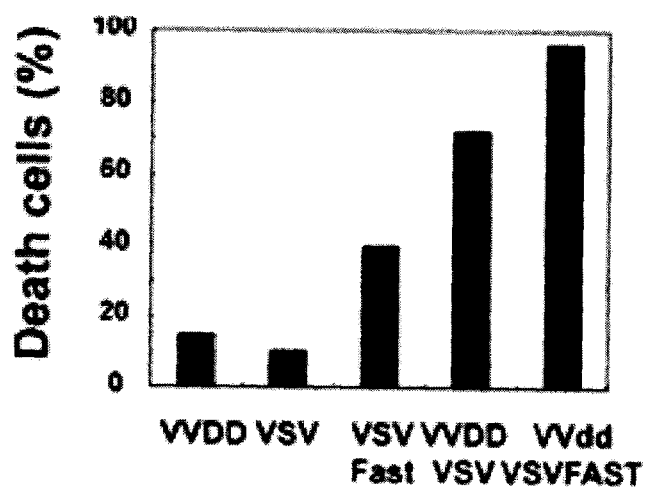

75% confluent 786-O renal cancer cells were left untreated or treated with VVDD-eGFP (0.1 MOI) for 2 hours and VSVFAST-DsRed (0.1 MOI) infection was then performed or not for 45 minutes. eGFP (VV) and DsRed (VSVFAST) fluorescence were detected at 48 hours by microscopy after VSVFAST infection. As shown in FIG. 8A, VVDD and VSVFAST titers were determined 48 hours after infection. As shown in FIG. 8B, an isobologram analysis was conducted; briefly, 786-O cells were treated with serial dilutions of VVDD followed by VSVFAST (fixed ratio of 1:100 PFU) in 96-well plates and processed as described herein. 72 hours following VSVFAST infection, viral oncolytic effect was assessed by a crystal violet assay demonstrating massive cell death in double-treated conditions. As shown in FIG. 8C, the percentage of cell death was assessed. 786-O cells were treated with Vaccinia virus followed by VSV or VSVFAST. Cytotoxicity was assessed using MTS reagent after 72 hours. 75% confluent 786-O renal cancer cells were left untreated or treated with VVDD (0.1 MOI) for 2 hours and/or VSVFAST without any tag (0.1 MOI) for 45 minutes. eGFP (VV) fluorescence was detected at 48 hours after infection. Further, patient colon tumour specimen was infected by VVDD (eGFP) for 2 hours with 1.10e7 pfu and/or VSVFAST (DsRed) with 1.10e8 pfu for 45 minutes. eGFP and DsRed expression was monitored after viral inoculation.

Example 9: Jx-963 and Jx-594 Enhance VSVΔ51

JX-963 is a Western Reserve strain of vaccinia [WR] with deletions in the viral thymidine kinase [TK] and vaccinia growth factor [VGF] genes and expressing human GM-CSF (Thorn et al., J. Clin. Invest. 117:3350-3358 (2007)). JX-594 is a TK-deleted vaccinia expressing GM-CSF (Liu et al., Molecular Therapy (2008) 16 (9), 1637-1642; Kim et al., Molecular Therapy (2006) 14, 361-370).

75% confluent 786-O renal cancer cells were left untreated or treated with VVDD-eGFP, JX594-eGFP or JX-963-eGFP (0.1 MOI) for 2 hours and with VSV-DsRed (0.1) infection was then performed or not for 45 minutes. eGFP (VVs) and DsRed (VSV) fluorescence were detected at 48 hours by microscopy after VSV infection.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s), publications, database or internet resources and references, including but not limited to patents and patent applications, cited in this specification are incorporated herein by reference as if each individual publication were specifically and individually indicated to be incorporated by reference herein and as though fully set forth herein. The invention includes all embodiments and variations substantially as described herein, with reference to the examples and drawings.

REFERENCES

Citation of the following references is not an admission that such references are prior art to with respect to the subject matter disclosed herein. The following documents are incorporated herein by reference, as if each were specifically and individually indicated to be incorporated by reference herein and as though fully set forth herein:

Aghi, M. & Martuza, R. L. Oncolytic viral therapies—the clinical experience. *Oncogene* 24, 7802-7816 (2005).

Ahmed, M., Cramer, S. D. & Lyles, D. S. (2004) Sensitivity of prostate tumors to wild type and M protein mutant vesicular stomatitis viruses. Virology 330, 34-49.

Alcami, A. & Smith, G. L. Vaccinia, cowpox, and camelpox viruses encode soluble gamma interferon receptors with novel broad species specificity. *J Virol* 69, 4633-4639 (1995).

Alcami, A., Symons, J. A. & Smith, G. L. The vaccinia virus soluble alpha/beta interferon (IFN) receptor binds to the cell surface and protects cells from the antiviral effects of IFN. *J Virol* 74, 11230-11239 (2000).

Altomonte, J., Wu, L., Chen, L., Meseck, M., Ebert, O., Garcia-Sastre, A. et al. (2008) Exponential Enhancement of Oncolytic Vesicular Stomatitis Virus Potency by Vector-mediated Suppression of Inflammatory Responses In Vivo. Mol. Ther. 16, 146-153.

Arita, et al., 1985, in Vaccinia Viruses as Vectors for Vaccine Antigens, ed. Quinnan, J. (Elsevier, New York), pp. 49-60.

Bell et al. (2003) Getting oncolytic virus therapies off the ground. Cancer Cell. 4(1): 7-11.

Bell, J. C. Oncolytic viruses: what's next? *Curr Cancer Drug Targets* 7, 127-131 (2007).

Breitbach, C. J. et al. Targeted inflammation during oncolytic virus therapy severely compromises tumor blood flow. *Mol Ther* 15, 1686-1693 (2007).

Brown, C. W. et al. The p14 FAST protein of reptilian reovirus increases vesicular stomatitis virus neuropathogenesis. *J Virol* 83, 552-561 (2009).

Buller et al., 1988, Virology 164: 182-192

Chang, H.-M. et al. (2004) Induction of interferon-stimulated gene expression and antiviral responses require protein deacetylase activity. Proc Natl. Acad. Sci. U.S.A. 101(26): 9578-9583.

Chiocca, E. A. et al. (2004). A phase I open-label, dose-escalation, multi-institutional trial of injection with an E1B-attenuated adenovirus, ONYX-015, into the peritumoral region of recurrent malignant gliomas, in the adjuvant setting. Mol. Ther. 10, 958-966.

Chou, T. C. Theoretical basis, experimental design, and computerized simulation of synergism and antagonism in drug combination studies. *Pharmacol Rev* 58, 621-681 (2006).

Clancy, E. K. & Duncan, R. Reovirus FAST protein transmembrane domains function in a modular, primary sequence-independent manner to mediate cell-cell membrane fusion. *J Virol* 83, 2941-2950 (2009).

Colamonici, O. R., Domanski, P., Sweitzer, S. M., Lamer, A. & Buller, R. M. Vaccinia virus B18R gene encodes a type I interferon-binding protein that blocks interferon alpha transmembrane signaling. *J Biol Chem* 270, 15974-15978 (1995).

Conzelmann, K. K. (1998) Nonsegmented negative-strand RNA viruses: genetics and manipulation of viral genomes. Annu. Rev. Genet. 32, 123-162.

Corcoran J. A., & Duncan, R. (2004) Reptilian reovirus utilizes a small type III protein with an external myristylated amino terminus to mediate cell-cell fusion. J. Virol. 78, 4342-4351.

Crompton, A. M. & Kim, D. H. From ONYX-015 to armed vaccinia viruses: the education and evolution of oncolytic virus development. *Curr Cancer Drug Targets* 7, 133-139 (2007).

Ebert O. et al. (2004) Syncytia induction enhances the oncolytic potential of vesicular stomatitis virus in virotherapy for cancer. Cancer Res. 64, 3265-3270.

Everts and van der Poel H G (2005). Replication-selective oncolytic viruses in the treatment of cancer. Cancer Gene Ther. February; 12(2):141-161.

Filipowicz, W., Jaskiewicz, L., Kolb, F. A. & Pillai, R. S. (2005) Post-transcriptional gene silencing by siRNAs and miRNAs. Curr. Opin. Struct. Biol. 15, 331-341.

Fu, X. et al. (2007) Antitumor effects of two newly constructed oncolytic herpes simplex viruses against renal cell carcinoma. Int. J. Oncology 30(6), 1561-1567.

Gojo et al. (2007) Phase 1 and pharmacologic study of MS-275, a histone deacetylase inhibitor, in adults with refractory and relapse acute leukemias. Blood. 109(7); 2781-2790.

Haralambieva, I., Iankov, I., Hasegawa, K., Harvey, M., Russell, S. J. & Peng, K. W. (2007) Engineering oncolytic measles virus to circumvent the intracellular innate immune response. Mol. Ther. 15, 588-597.

Harrow, S. et al. (2004). HSV1716 injection into the brain adjacent to tumor following surgical resection of high-grade glioma: safety data and long-term survival. Gene Ther. 11, 1648-1658.

Hirasawa, K. et al. (2003). Systemic reovirus therapy of metastatic cancer in immune-competent mice. Cancer Res. 63, 348-353.

Hoffmann D., et al. (2008) Evaluation of twenty-one human adenovirus types and one infectivity-enhanced adenovirus for the treatment of malignant melanoma. J. Invest. Dermatol. 128, 988-998.

Hoffmann, D., Bangen, J. M., Bayer, W., Wildner, O. (2006) Synergy between expression of fusogenic membrane proteins, chemotherapy and facultative virotherapy in colorectal cancer. Gene Ther 13(21), 1534-1544.

Hoffmann, D., Wildner, O. (2006) Enhanced killing of pancreatic cancer cells by expression of fusogenic membrane glycoproteins in combination with chemotherapy. Mol. Cancer Ther. 5(8), 2013-2022.

Hoffmann, D., Grunwald, T., Kuate S., Wildner O. (2007) Mechanistic analysis and comparison of viral fusogenic membrane proteins for their synergistic effects on chemotherapy. Cancer Biol. Ther. 6(4), 510-518.

Hoffmann, D., Bayer, W., Wildner, O. (2007) Local and distant immune-mediated control of colon cancer growth with fosogenic membrane glycoproteins in combination with viral oncolysis. 18(5), 435-50.

Hummel, J. L., Safroneeva, E. & Mossman, K. L. (2005) The role of ICP0-Null HSV-1 and interferon signaling defects in the effective treatment of breast adenocarcinoma. Mol. Ther. 12, 1101-1110.

Ichihashi, Y. (1996) Extracellular enveloped vaccinia virus escapes neutralization. Virology 217, 478-485.

Jayakar, H. R., Murti, K. G. & Whitt, M. A. (2000) Mutations in the PPPY motif of vesicular stomatitis virus matrix protein reduce virus budding by inhibiting a late step in virion release. J. Virol. 74, 9818-9827.

Karube, Y., Tanaka, H., Osada, H., Tomida, S., Tatematsu, Y., Yanagisawa, K. et al. (2005) Reduced expression of Dicer associated with poor prognosis in lung cancer patients. Cancer Sci. 96, 111-115.

Kaufman, H. L. et al. (2005). Targeting the local tumor microenvironment with vaccinia virus expressing B7.1 for the treatment of melanoma. J. Clin. Invest. 115, 1903-1912.

Kim, D. Clinical research results with dl1520 (Onyx-015), a replication-selective adenovirus for the treatment of cancer: what have we learned? *Gene Ther* 8, 89-98 (2001).

Kopecky, S. A., Willingham, M. C. & Lyles, D. S. (2001) Matrix protein and another viral component contribute to induction of apoptosis in cells infected with vesicular stomatitis virus. J. Virol. 75, 12169-12181.

Kumar, S., Gao, L., Yeagy, B. & Reid, T. Virus combinations and chemotherapy for the treatment of human cancers. *Curr Opin Mol Ther* 10, 371-379 (2008).

Lane, et al., 1969, N. Engl. J. Med. 281, 1201-1208

Lichty, B. D., Power, A. T., Stojdl, D. F. & Belt, J. C. (2004) Vesicular stomatitis virus: re-inventing the bullet. Trends Mol. Med. 10, 210-216.

Liu, T. C., Galanis, E. & Kim, D. Clinical trial results with oncolytic virotherapy: a century of promise, a decade of progress. *Nat Clin Pract Oncol* 4, 101-117 (2007).

Liu, T. C. & Kim, D. Systemic efficacy with oncolytic virus therapeutics: clinical proof-of-concept and future directions. *Cancer Res* 67, 429-432 (2007).

Liu, T. C., Hwang, T., Park, B. H., Bell, J. & Kim, D. H. The targeted oncolytic poxvirus JX-594 demonstrates antitumoral, antivascular, and anti-HBV activities in patients with hepatocellular carcinoma. *Mol Ther* 16, 1637-1642 (2008).

Lorence, R. M. et al. (2003). Overview of phase I studies of intravenous administration of PV701, an oncolytic virus. Curr. Opin. Mol. Ther. 5, 618-624.

Lorence, R. M. et al. (2005). Continuing the interaction between non-clinical and clinical studies. Third International Meeting on Oncolytic Virus Therapeutics: Banff, Alberta (12 Mar. 2005);

Mastrangelo, M. J. et al. (1999) Intratumoral recombinant GM-CSF-encoding virus as gene therapy in patients with cutaneous melanoma. Cancer Gene Ther. 6(5), 409-422.

Mayr, C., Hemann, M. T. & Bartel, D. P. (2007) Disrupting the pairing between let-7 and Hmga2 enhances oncogenic transformation. Science 315, 1576-1579.

McCart et al. (2001). Systemic Cancer Therapy with a Tumor-selective Vaccinia Virus Mutant Lacking Thymidine Kinase and Vaccinia Growth Factor Genes. Cancer Research 61, 8751-8757)

McCart, J. A. et al. Oncolytic vaccinia virus expressing the human somatostatin receptor SSTR2: molecular imaging after systemic delivery using 111In-pentetreotide. Mol Ther 10, 553-561 (2004).

Mian et al. (2003) Fully Human Anti-Interleukin 8 Antibody Inhibits Tumor Growth in Orthotopic Bladder Cancer Xenografts via Down-Regulation of Matrix Metalloproteases and Nuclear Factor-{kappa}B Clin. Cancer Res., Aug. 1, 2003; 9(8): 3167-3175.

Moss, B. & Earl, P. L. Overview of the vaccinia virus expression system. *Curr Protoc Protein Sci* Chapter 5, Unit 5 11 (2001).

Moss, B. Poxvirus entry and membrane fusion. *Virology* 344, 48-54 (2006).

Muster, T., Rajtarova, J., Sachet, M., Unger, H., Fleischhacker, R., Romirer, I. et al. (2004) Interferon resistance promotes oncolysis by influenza virus NS1-deletion mutants. Int. J. Cancer 110, 15-21.

Myers, R. et al. (2005). Oncolytic activities of approved mumps and measles vaccines for therapy of ovarian cancer. Cancer Gene Ther. 12, 593-599.

Naik, A. M. et al. Intravenous and isolated limb perfusion delivery of wild type and a tumor-selective replicating mutant vaccinia virus in nonhuman primates. *Hum Gene Ther* 17, 31-45 (2006).

Nakamori M., et al. Effective therapy of metastatic ovarian cancer with an oncolytic herpes simplex virus incorporating two membrane fusion mechanisms. Clin. Cancer Res. 9, 2727-2733.

Ogawa F. et al. (2008) Combined oncolytic virotherapy with herpes simplex virus for oral squamous cell carcinoma. Anticancer Res. 28, 3637-3645.

Otsuka, M., Jing, Q., Georgel, P., New, L., Chen, J., Mols, J. et al. (2007) Hypersusceptibility to vesicular stomatitis virus infection in Dicer1-deficient mice is due to impaired miR24 and miR93 expression. Immunity. 27, 123-134.

Parato at al. (2005). Recent progress in the battle between oncolytic viruses and tumors. Nat Rev Cancer. 5(12): 965-76.

Parato, K. A., Senger, D., Forsyth, P. A. & Bell, J. C. (2005) Recent progress in the battle between oncolytic viruses and tumours. Nat. Rev. Cancer 5, 965-976.

Park, B. H. et al. Use of a targeted oncolytic poxvirus, JX-594, in patients with refractory primary or metastatic liver cancer: a phase I trial. Lancet Oncol 9, 533-542 (2008).

Parr, M. J. et al. Tumor-selective transgene expression in vivo mediated by an E2F-responsive adenoviral vector. *Nat Med* 3, 1145-1149 (1997).

Pecora, A. L. et al. (2002) Phase I trial of intravenous administration of PV701, an oncolytic virus, in patients with advanced solid cancers. J. Clin. Oncol. 20, 2251-2266.

Power, A. T. at al. Carrier cell-based delivery of an oncolytic virus circumvents antiviral immunity. *Mol Ther* 15, 123-130 (2007).

Reid at al. (2002). Intravascular adenoviral agents in cancer patients: lessons from clinical trials. Cancer Gene Ther. 9, 979-986.

Reid, T. et al. (2001). Intra-arterial administration of a replication selective adenovirus (dl1520) in patients with colorectal carcinoma metastatic to the liver: a phase I trial. Gene Ther. 8, 1618-1626.

Ries S J, Brandts C H. (2004) Oncolytic viruses for the treatment of cancer: current strategies and clinical trials. Drug Discov. Today 2004 Sep. 1; 9(17):759-768.

Russell, S. J. & Peng, K. W. Viruses as anticancer drugs. *Trends Pharmacol Sci* 28, 326-333 (2007).

Scherr, M. & Eder, M. (2007) Gene silencing by small regulatory RNAs in mammalian cells. Cell Cycle 6, 444-449.

Schnell, M. J., Buonocore, L., Kretzschmar, E., Johnson, E. & Rose, J. K. (1996) Foreign glycoproteins expressed from recombinant vesicular stomatitis viruses are incorporated efficiently into virus particles. Proc. Natl. Acad. Sci. U.S.A. 93, 11359-11365.

Shah et al., (2003). Oncolytic viruses: clinical applications as vectors for the treatment of malignant gliomas. J. Neurooncol. 65, 203-226.

Shin E J et al. (2007) Fusogenic vesicular stomatitis virus for the treatment of head and neck squamous carcinomas. Otolaryngol. Head Neck Surgery 136, 811-817.

Shors S. T. et al., (1998) Role of the vaccinia virus E3L and K3L gene products in rescue of VSV and EMCV from the effects of IFN-alpha. J. Interferon Cytokine Res. 18, 721-729.

Stojdl, D. F., Lichty, B., Knowles, S., Marius, R., Atkins, H., Sonenberg, N. et al., (2000) Exploiting tumor-specific defects in the interferon pathway with a previously unknown oncolytic virus. Nat. Med. 6, 821-825.

Stojdl, D. F., Lichty, B. D., tenOever, B. R., Paterson, J. M., Power, A. T., Knowles, S. et al., (2003) VSV strains with defects in their ability to shutdown innate immunity are potent systemic anti-cancer agents. Cancer Cell 4, 263-275.

Stojdl, D. F. et al. Exploiting tumor-specific defects in the interferon pathway with a previously unknown oncolytic virus. *Nat Med* 6, 821-825 (2000).

Symons, J. A., Alcami, A. & Smith, G. L. Vaccinia virus encodes a soluble type I interferon receptor of novel structure and broad species specificity. *Cell* 81, 551-560 (1995).

Taneja, S., MacGregor, J., Markus, S., Ha, S. & Mohr, I. (2001) Enhanced antitumor efficacy of a herpes simplex virus mutant isolated by genetic selection in cancer cells. Proc. Natl. Acad. Sci. U.S.A. 98, 8804-8808.

Thorne, S. H. & Contag, C. H. Combining immune cell and viral therapy for the treatment of cancer. *Cell Mol Life Sci* 64, 1449-1451 (2007).

Thorne, S. H. et al. Rational strain selection and engineering creates a broad-spectrum, systemically effective oncolytic poxvirus, JX-963. *J Clin Invest* 117, 3350-3358 (2007).

U.S. Pat. No. 7,431,929 (Jacobs et al.)

Vaha-Koskela, M. J. et al. A novel neurotropic expression vector based on the avirulent A7(74) strain of Semliki Forest virus. *J Neurovirol* 9, 1-15 (2003).

Vaha-Koskela, M. J. et al. Oncolytic capacity of attenuated replicative semliki forest virus in human melanoma xenografts in severe combined immunodeficient mice. *Cancer Res* 66, 7185-7194 (2006).

Valencia-Sanchez, M. A., Liu, J., Hannon, G. J. & Parker, R. (2006) Control of translation and mRNA degradation by miRNAs and siRNAs. Genes Dev. 20, 515-524.

Vancova, I., La Bonnardiere, C. & Kontsek, P. Vaccinia virus protein B18R inhibits the activity and cellular binding of the novel type interferon-delta. *J Gen Virol* 79 (Pt 7), 1647-1649 (1998).

Varghese, S. & Rabkin, S. D. (2002) Oncolytic herpes simplex virus vectors for cancer virotherapy. Cancer Gene Ther. 9, 967-978.

Vigil A. et al. (2007) Use of reverse genetics to enhance the oncolytic properties of Newcastle disease virus. Cancer Res. 67, 8285-8292.

Villarreal, L. P., Breindl, M. & Holland, J. J. (1976) Determination of molar ratios of vesicular stomatitis virus induced RNA species in BHK21 cells. Biochemistry 15, 1663-1667.

Whitaker-Dowling, P., & Youngner J. S. (1983) Vaccinia rescue of VSV from interferon-induced resistance: reversal of translation block and inhibition of protein kinase activity. Virology 131, 128-136.

Whitaker-Dowling, P. & Youngner, J. S. (1988) Vaccinia virus stimulates the growth of vesicular stomatitis virus at the level of protein synthesis in mouse L cells. Virus Res. 10, 215-224.

Xia, Z. J. et al. (2004). Phase III randomized clinical trial of intratumoral injection of E1B gene-deleted adenovirus (H101) combined with cisplatin-based chemotherapy in treating squamous cell cancer of head and neck or esophagus. Ai Zheng 23, 1666-1670.

The invention claimed is:

1. A method of inducing a contemporaneous synergistic oncolytic infection of a cancer cell, said method comprising infecting the cancer cell with
   (i) an effective amount of an oncolytic vaccinia virus (VV) expressing a functional vaccinia virus type 1 interferon (IFN) binding protein comprising the amino acid sequence as set forth in SEQ ID NO: 2, wherein the VV does not express functional thymidine kinase and functional vaccinia growth factor; and,
   (ii) an effective amount of an IFN-sensitive oncolytic vesicular stomatitis virus (VSV) comprising a mutation in the gene encoding matrix (M) protein rendering the encoded polypeptide unable to block IFN gene expression, wherein the oncolytic VSV has an attenuating deletion of methionine 51 of the matrix protein (VS-VdeltaM51);
   wherein the cancer cell is infected with the VV before the oncolytic VSV, and wherein the cancer cell is selected from the group consisting of a liver, colon, ovarian, kidney, rectal, endometrial, brain, pancreatic, lung, breast, sarcoma and groin cancer cell,
   thereby inducing a contemporaneous synergistic oncolytic infection of cancer cells by the viruses.

2. The method of claim 1, wherein the cancer cell is in a human subject.

3. The method of claim 1, wherein the genome of the oncolytic VSV does not encode type 1 interferon (IFN) binding protein.

4. The method of claim 1, wherein the VV expresses GM-CSF.

5. The method of claim 1, wherein the oncolytic VSV has a genome encoding a reovirus Fusion Associated Small Transmembrane (FAST) protein, wherein the p14 protein has the amino acid sequence set forth as SEQ ID NO:1.

6. The method of claim 1 wherein the VV lacks a functional E3L gene.

* * * * *

SEQUENCE LISTING

```
<160> NUMBER OF SEQ ID NOS: 2

<210> SEQ ID NO 1
<211> LENGTH: 125
<212> TYPE: PRT
<213> ORGANISM: Reovirus
<220> FEATURE:
<221> NAME/KEY: AAP03134
<222> LOCATION: (1)..(125)
<223> OTHER INFORMATION: Reptilian reovirus p14 Fusion Associated Small
      Transmembrane (FAST) protein
<300> PUBLICATION INFORMATION:
<301> AUTHORS: Duncan,R., Corcoran,J., Shou,J. and Stoltz,D.
<302> TITLE: Reptilian reovirus: a new fusogenic orthoreovirus species
<303> JOURNAL: Virology
<304> VOLUME: 319
<305> ISSUE: 1
<306> PAGES: 131-140
<307> DATE: 2004
<308> DATABASE ACCESSION NUMBER: AAPo3134
<309> DATABASE ENTRY DATE: 2004-06-22
<313> RELEVANT RESIDUES IN SEQ ID NO: (1)..(125)
<300> PUBLICATION INFORMATION:
<301> AUTHORS: Duncan,R., Corcoran,J., Shou,J. and Stoltz,D.
<302> TITLE: Reptilian reovirus: a new fusogenic orthoreovirus species
<303> JOURNAL: Virology
<304> VOLUME: 319
<305> ISSUE: 1
<306> PAGES: 131-140
<307> DATE: 2004
<308> DATABASE ACCESSION NUMBER: AAP03134
<309> DATABASE ENTRY DATE: 2004-06-22
<313> RELEVANT RESIDUES IN SEQ ID NO: (1)..(125)

<400> SEQUENCE: 1

Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile Ala Gly Leu Val Ala Leu Leu Thr
        35                  40                  45

Phe Leu Ala Phe Gly Phe Trp Leu Phe Lys Tyr Leu Gln Lys Arg Arg
    50                  55                  60

Glu Arg Arg Arg Gln Leu Thr Glu Phe Gln Lys Arg Tyr Leu Arg Asn
65                  70                  75                  80

Ser Tyr Arg Leu Ser Glu Ile Gln Arg Pro Ile Ser Gln His Glu Tyr
                85                  90                  95

Glu Asp Pro Tyr Glu Pro Pro Ser Arg Arg Lys Pro Pro Pro Pro
                100                 105                 110
```

Tyr Ser Thr Tyr Val Asn Ile Asp Asn Val Ser Ala Ile
            115                 120                 125

<210> SEQ ID NO 2
<211> LENGTH: 351
<212> TYPE: PRT
<213> ORGANISM: Vaccinia virus
<220> FEATURE:
<221> NAME/KEY: BAA00826
<222> LOCATION: (1)..(351)
<223> OTHER INFORMATION: Vaccinia virus Western Reserve strain B18R
      protein.
<300> PUBLICATION INFORMATION:
<301> AUTHORS: Goebel,S.J., Johnson,G.P., Perkus,M.E., Davis,S.W.,
      Winslow,J.P. and Paoletti,E.
<302> TITLE: The complete DNA sequence of vaccinia virus
<303> JOURNAL: Virology
<304> VOLUME: 179
<305> ISSUE: 1
<306> PAGES: 247-266
<307> DATE: 1990
<308> DATABASE ACCESSION NUMBER: BAA00826
<309> DATABASE ENTRY DATE: 2005-06-20
<313> RELEVANT RESIDUES IN SEQ ID NO: (1)..(351)

<400> SEQUENCE: 2

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

```
Thr Ala Val Ser Thr Ser Leu Leu Ile Asp Asp Val Leu Ile Glu Trp
            275                 280                 285

Glu Asn Pro Ser Gly Trp Leu Ile Gly Phe Asp Phe Asp Val Tyr Ser
        290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
            340                 345                 350
```